United States Patent
Greenhalgh

[19]

[11] Patent Number: 6,159,239
[45] Date of Patent: Dec. 12, 2000

[54] WOVEN STENT/GRAFT STRUCTURE

[75] Inventor: E. Skott Greenhalgh, Wyndmoor, Pa.

[73] Assignee: Prodesco, Inc., Perkasie, Pa.

[21] Appl. No.: 09/134,192

[22] Filed: Aug. 14, 1998

[51] Int. Cl.[7] .................................................. A61F 2/06
[52] U.S. Cl. .................. 623/1.13; 623/1.22; 623/1.53; 623/1.35
[58] Field of Search ............................... 623/1.13, 1.22, 623/1.35, 1.37, 1.51, 1.53, 1.54, 12; 606/198, 194

[56] References Cited

U.S. PATENT DOCUMENTS

| | | |
|---|---|---|
| 1,609,152 | 11/1926 | Carmel . |
| 1,847,262 | 3/1932 | Reuter . |
| 1,878,620 | 9/1932 | Bunnell et al. . |
| 2,190,793 | 2/1940 | Lombardi . |
| 3,087,699 | 4/1963 | Foster . |
| 3,404,384 | 10/1968 | Snyder . |
| 3,479,670 | 11/1969 | Medell . |
| 4,130,904 | 12/1978 | Whalen . |
| 4,313,231 | 2/1982 | Koyamada . |
| 4,654,748 | 3/1987 | Rees . |
| 4,787,899 | 11/1988 | Lazarus . |
| 4,899,543 | 2/1990 | Romanelli et al. . |
| 4,969,896 | 11/1990 | Shors . |
| 5,084,065 | 1/1992 | Weldon et al. . |
| 5,370,682 | 12/1994 | Schmitt . |
| 5,370,683 | 12/1994 | Fontaine ................................. 623/1 |
| 5,385,580 | 1/1995 | Schmitt . |
| 5,405,377 | 4/1995 | Cragg . |
| 5,496,364 | 3/1996 | Schmitt . |
| 5,507,767 | 4/1996 | Maeda et al. . |
| 5,507,771 | 4/1996 | Gianturco . |
| 5,509,931 | 4/1996 | Schmitt . |
| 5,549,663 | 8/1996 | Cottone, Jr. . |
| 5,556,414 | 9/1996 | Turi . |
| 5,556,426 | 9/1996 | Popadiuk et al. . |
| 5,562,725 | 10/1996 | Schmitt et al. . |
| 5,571,173 | 11/1996 | Parodi . |
| 5,578,071 | 11/1996 | Parodi . |
| 5,591,195 | 1/1997 | Taheri et al. . |
| 5,591,198 | 1/1997 | Boyle et al. ........................... 606/198 |
| 5,628,783 | 5/1997 | Quiachon et al. . |
| 5,628,788 | 5/1997 | Pinchuk . |
| 5,667,523 | 9/1997 | Bynon et al. . |
| 5,674,277 | 10/1997 | Freitag . |
| 5,683,448 | 11/1997 | Cragg . |
| 5,697,970 | 12/1997 | Schmitt et al. . |
| 5,855,598 | 1/1999 | Pinchuk ...................................... 623/1 |
| 5,876,432 | 3/1999 | Lau et al. .................................... 623/1 |

FOREIGN PATENT DOCUMENTS

| | | |
|---|---|---|
| 0536735 | 4/1993 | European Pat. Off. . |
| 0263392 | 4/1998 | European Pat. Off. . |
| WO 92/16166 | 10/1992 | WIPO . |
| WO 97/21403 | 6/1997 | WIPO . |
| WO 97/25002 | 7/1997 | WIPO . |

*Primary Examiner*—Michael J. Milano
*Assistant Examiner*—Hieu Phan
*Attorney, Agent, or Firm*—Baker Botts L.L.P.

[57] ABSTRACT

A combined stent/graft structure for repair of a body tube in a living body. The structure includes a textile graft adapted to enhance fluid integrity of the body tube and a stent expandable between a first position permitting easy insertion of the stent into the body tube and a second position wherein the stent presses securely against the inside surface of the body tube. The stent includes a first elongate wire-shaped stent member with both a stent member global axis and a stent member local axis, and is integrally secured to the graft by at least one graft yarn of which the graft is formed. Substantial portions of the first stent member global axis form a non-orthogonal angle with the graft main portion axis when projected into a plane containing the graft main portion axis. A woven textile is also part of the invention as is a method of manufacturing such a woven textile, which can be used to produce stent/graft structures according to the invention.

42 Claims, 23 Drawing Sheets

WOVEN STENT/GRAFT STRUCTURE

BACKGROUND OF THE INVENTION

1. Field of the Invention

The present invention relates to tubular prostheses for use in a living body, and more particularly, to a combined stent/graft structure wherein a stent member is integrally secured to a textile graft by at least one yarn from which the graft is formed.

2. Brief Description of the Prior Art

Vascular graft techniques have been known for approximately 30 years. Knitted or woven tubes are formed from fibrous materials and are employed to repair a damaged body tube, such as a damaged vascular structure. Patients with diseased or damaged vascular structures, or other body tubes, can be successfully treated with such graft structures. For example, a patient with an abdominal aortic aneurysm can have the aneurysm repaired with a suitable graft. However, pure graft structures, although designed to enhance fluid integrity of the damaged body tube, do not have the capability to support themselves or to be secured in place. Thus, invasive surgery is required to attach the structures to the damaged vascular area, which may result in a long, expensive hospital stay and attendant dangers due to the major surgery required.

In an effort to overcome the problems with graft structures, an alternative approached was developed in the early 1980s. So-called stents were developed which could expand a clogged artery, for example, and be self-securing by virtue of an interference fit with the artery wall. Such structures might be self-expanding, by virtue of recovery of elastic stress, or might be formed of ductile materials and expanded with a balloon catheter. However, so-called stent structures do not in themselves enhance the fluid integrity of the body tube. They rely on the diseased wall of the body tube to maintain fluid integrity, and are directed primarily to expanding the body tube such as, for example, a clogged artery.

Recently, devices have been developed which combine the benefits of both graft and stent structures. In these types of devices, a stent structure is secured to a graft structure. The graft structure serves to enhance fluid integrity of the body tube, while the stent structure helps to support the graft and to secure the graft in place against the body tube. These types of devices can be implanted with a catheter procedure, and thus do not require invasive surgery.

U.S. Pat. No. 4,130,904 to Whalen, U.S. Pat. No. 4,313,231 to Koyamada, U.S. Pat. No. 5,507,767 to Maeda et al., U.S. Pat. No. 5,591,195 to Thaeri et al., U.S. Pat. No. 5,667,523 to Bynon et al., and U.S. Pat. No. 5,674,277 to Freitag all disclose combined stent/graft structures. Although these structures have significantly enhanced patient treatment, a number of problems still remain. Heretofore, most combined stent/graft structures have fastened the stent to the graft via suturing or glue. These methods are problematic. Suturing may not be repeatable for quality control, can be unreliable, resulting in potential loosening of the stent from the graft, with catastrophic results for the patient, and may degrade fluid integrity of the graft due to the needle holes required for the suturing. Gluing may also be unreliable and may pose repeatability and quality control problems as well. U.S. Pat. Nos. 5,571,173 and 5,578,071, both to Parodi, show a graft structure with an undulating wire which is woven into the graft. The wire is confined to an end of the graft structure, and is made of a ductile material. It must be expanded by a balloon catheterization procedure. The Parodi patents suggest that the stent can be woven into the interior of the graft, but provide no details as to how this can be accomplished. Further, the undulating wire of Parodi appears to have a global axis which is parallel to the fill yarns of the graft, and thus, could not be extended over the whole length of the graft structure.

In view of the deficiencies of prior art devices, it would be desirable to provide a stent/graft structure wherein the stent is integrally secured to the graft in a manner which does not compromise fluid integrity, is reliable, and is repeatable for quality control purposes. It would also be desirable if the stent member in the combined structure is secured in a way which lent itself to easy manufacturing. Yet further, it would be desirable if a global axis of the stent member could describe a generally helical path with respect to the graft structure, such that a single stent member could extend substantially over the whole length of the graft, thus providing support throughout the length of the graft.

SUMMARY OF THE INVENTION

The present invention, which addresses the needs of the prior art, provides a combined stent/graft structure for repair of a body tube in a living body. The structure includes a textile graft adapted to enhance fluid integrity of the body tube. The graft is a generally tubular graft main portion with a graft main portion axis and first and second graft main portion ends, and is formed, at least in part, by at least one graft yarn.

The device also includes a stent which is expandable between a first position permitting easy insertion of the stent into the body tube and a second position wherein the stent presses securely against the inside surface of the body tube. The stent includes at least a first elongate wire-shaped stent member which has a stent member global axis and a stent member local axis. The first stent member is integrally secured to the graft by the at least one graft yarn of which the graft is formed. Substantial portions of the first stent member global axis form a non-orthogonal angle with the graft main portion axis when projected into a plane containing the graft main portion axis. Thus, if desired, the stent can be manufactured so as to extend over a substantial portion of the length of the graft. The first stent member has material properties which are preselected to support the graft when it is in the second, or expanded, position. The local axis of the first stent member is generally defined by centroids of the adjacent cross-sections of the first stent member. The global axis is generally defined by a straight-line curve fit to the local axis in a coordinate system which is substantially coincident with the generally tubular graft main portion.

Multiple stent members having different properties can be employed.

In another aspect of the invention, a generally undulating stent member need not necessarily have its global axis non-orthogonal to the graft main portion axis. In this case, the textile graft is woven and the first stent member is secured by at least one warp yarn at each of a plurality of interweave points spaced circumferentially about the graft. The interweave points are separated from each other by a predetermined number of the warp yarns. Securing with fill yarns is also possible.

The present invention further provides a method of forming a textile with an undulating wire member therein. The method takes advantage of so-called shape memory materials. The method includes forming a wire which exhibits shape memory behavior into an undulating wire member, training the wire to remember its shape while it is formed into the undulating wire member, and causing the undulating wire member to straighten by undergoing a shape-memory transformation, so as to result in a straightened wire which retains a memory of an undulating shape. The method further includes securing the straightened wire into a conventional textile and then causing the straightened wire to undergo a shape memory transformation back to the remembered undulating shape.

The present invention further provides a woven textile with a plurality of warp yarns and a plurality of substantially orthogonal fill yarns which form a base fabric. The woven textile also includes an elongate wire-shaped structural member with both a member global axis and a member local axis. As before, the local axis is generally defined by centroids of adjacent cross-sections of the structural member and the global axis is generally defined by a straight-line curve fit to the member local axis, in this case, in a coordinate system which is substantially coplanar with the warp and fill yarns. The structural member is integrally secured to the base fabric at a plurality of interweave points and is secured by at least one warp yarn or at least one fill yarn at each of the interweave points. The interweave points are separated by a predetermined number of fill yarns and a predetermined number of warp yarns. These two parameters together determine a substantially non-orthogonal angle $\alpha$ between the member global axis and the warp yarns, and a complimentary substantially non-orthogonal angle $\beta=90°-\alpha$ a between the member global axis and the fill yarns. Such a woven textile can be employed to create stent/graft structures of the present invention, and is useful for other applications as well.

The present invention further provides a method of manufacturing a woven textile which has a structural member integrally woven therein. The method can be carried out using existing looms, with modifications to be set forth herein. The method includes providing a plurality of warp yarns; displacing a first group of the warp yarns in a first vertical direction relative to a second group of warp yarns to create a first shed between the first and second groups of warp yarns; and passing a weft insertion shuttle through the first shed, in a first weft shuttle direction, to form a weft yarn. The method further includes displacing a third group of the warp yarns in a second vertical direction relative to a fourth group of the warp yarns, to create a second shed between the third and fourth groups of warp yarns; passing the weft insertion shuttle through the second shed in a second weft shuttle direction which is opposed to the first weft shuffle direction, to form an additional weft yarn; and then repeating the aforementioned displacing and passing steps a predetermined number of times to obtain a predetermined number of weft yarns. The method further includes subsequently displacing at least a first single given warp yarn in one of the first and second vertical directions, relative to the remainder of the warp yarns, in order to create a structural member receiving gap; subsequently passing a structural member insertion shuttle through the structural member receiving gap in a first horizontal direction to dispense a wire-like structural member into the receiving gap; and then subsequently replacing the at least first single given warp yarn to secure the structural member.

The method further includes subsequently displacing all the warp yarns in an identical vertical direction; and then passing the structural member insertion shuttle past the warp yarns without interweaving with the warp yarns. The aforementioned displacing and passing steps are then again repeated to again obtain the desired predetermined number of weft yarns, and the steps associated with dispensing and securing the wire-like structural member are again repeated, using at least a second given single warp yarn which is spaced from the at least first given warp yarn used during the first securing by a predetermined distance. The predetermined distance and the predetermined number of fill yarns together define a non-orthogonal angle between the structural member and the warp yarns, and a complimentary non-orthogonal angle between the structural member and the weft yarns.

A method of manufacturing a woven textile wherein the structural member is secured with one or more weft yarns is also disclosed.

Yet further, the present invention provides a weaving shuttle for use in dispensing weft yarns when weaving with a loom. The weaving shuttle is particularly adapted for inserting the structural member previously described. The shuttle can include a main body portion adapted to move in a transverse direction through a shed formed of warp yarns on the loom and a spool which is mounted for rotation with respect to the main body portion about an axis substantially perpendicular to the transverse direction and substantially parallel to the warp yarns. The spool can be adapted to store the weft yarns and to dispense the weft yarns when the main body portion moves through the shed. It is envisioned that the weaving shuttle would primarily be used not for dispensing ordinary weft yarns, although this would be possible, but, as noted, would ordinarily be used for dispensing a structural member.

Still further, the present invention provides an alternative type of weaving shuttle which includes a main body portion adapted to move in a transverse direction through a shed formed of warp yarns on a loom; a spool mounted to the main body portion and having an axis substantially perpendicular to the transverse direction and substantially parallel to the warp yarn. The spool can be adapted to store the weft yarn and to dispense the weft yarn in a direction generally parallel to the spool axis when the main body portion moves through the shed. The weaving shuttle can also include a weft yarn guide which is secured to the main body portion and positioned to receive the weft yarn as it is dispensed from the spool and to guide the weft yarn into a direction substantially parallel to the transverse direction in which the main body portion moves. Again, this weaving shuttle, although it could be employed for ordinary weft yarns, is envisioned to be of particular use in dispensing the structural member in the manufacturing process set forth above.

These and other features and advantages of the present invention will become apparent from the following description of the preferred embodiments and the accompanying drawings, and the scope of the invention will be pointed out in the appended claims.

DETAILED DESCRIPTION OF THE PREFERRED EMBODIMENTS

Figure 1:
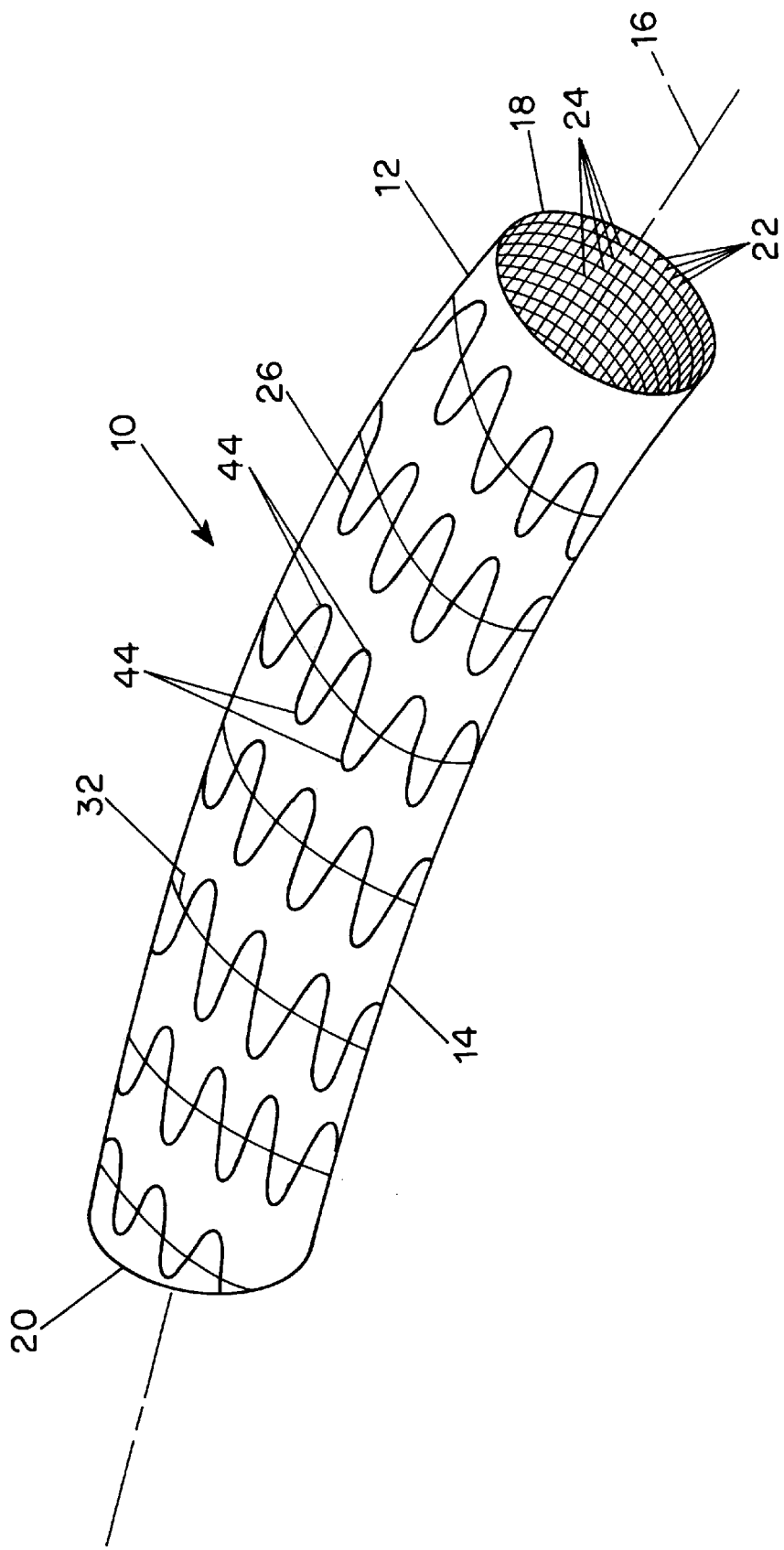
FIG. 1 shows a stent/graft structure in accordance with the present invention.

Reference should now be had to FIG. 1, which depicts a stent/graft structure according to the present invention, designated generally as 10. Structure 10 is adapted for repair of a body tube in a living body. The body tube has an inner surface; an example will be set forth below. The combined stent/graft structure 10 includes a textile graft 12 which is adapted to enhance fluid integrity of the body tube. The language "adapted to enhance fluid integrity of the body tube" is intended to distinguish from pure stent structures which rely on the body tube per se to maintain fluid integrity. The textile graft 12 is not, however, limited to a graft which is fluid-tight in and of itself; somewhat porous textiles which "grow into" the surrounding body tube to enhance fluid integrity are also contemplated. The graft 12 has a generally tubular graft main portion 14. Graft main portion 14 has a graft main portion axis 16 and first and second graft main portion ends 18, 20 respectively. Graft main portion 14 is formed, at least in part, by at least one graft yarn. The textile graft 12 can be formed in any manner, such as weaving, knitting, or braiding. A plain-woven embodiment is depicted in FIG. 1, for exemplary purposes. In this case, the at least one graft yarn could include a plurality of warp yarns 22 and a plurality of fill or weft yarns 24.

Structure 10 also includes a stent which is expandable between a first position which permits easy insertion of the stent into the body tube and a second position wherein the stent presses securely against the inside surface of the body tube. An example will be provided below. The stent in turn includes a first elongate wire-shaped stent member 26 which has both a first stent member global axis and a first stent member local axis.

Figure 2:
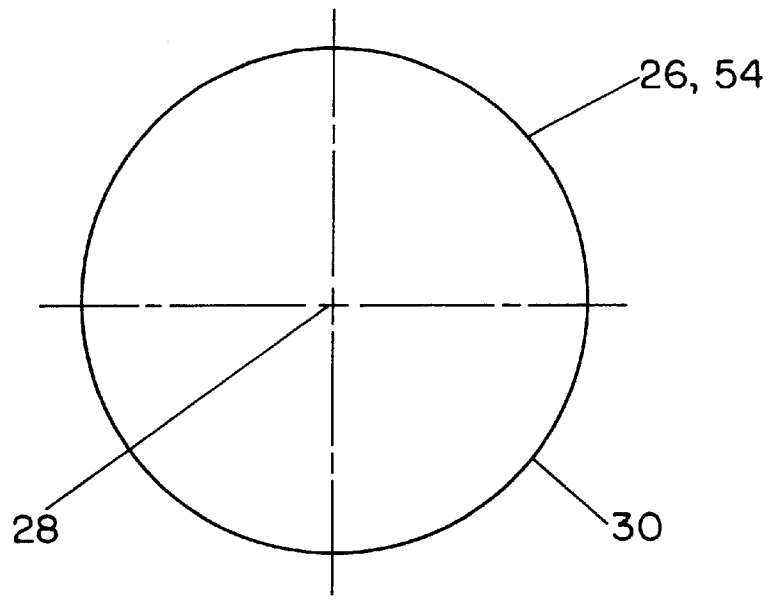
FIG. 2 shows a cross section through a stent member, including the centroid thereof.

With reference now to FIG. 2, the first stent member 26 has a local axis, projecting from the plane of the paper in FIG. 2, which is generally defined by the centroids 28 of adjacent cross-sections 30 of the first stent member 26. Since the first stent member 26 is depicted as having a relatively small thickness in FIG. 1, the first stent member local axis can be envisioned in FIG. 1 by simply looking at the shape of the first stent member 26. The first stent member global axis 32 is generally defined by a straight-line curve fit to the first stent member local axis, defined by centroids 28, in a coordinate system which is substantially coincident with the generally tubular graft main portion 14.

The description of locations of yarns and the like with the respect to such a coordinate system is known in the art, as set forth, for example, in page 4–13 of the *Atkins & Pearce Handbook of Industrial Braiding* authored by Drs. Frank Ko and Christopher Pastore and available from Atkins & Pearce, 3865 Madison Pike Covington, Kent. 41017 U.S.A.

Figure 3:
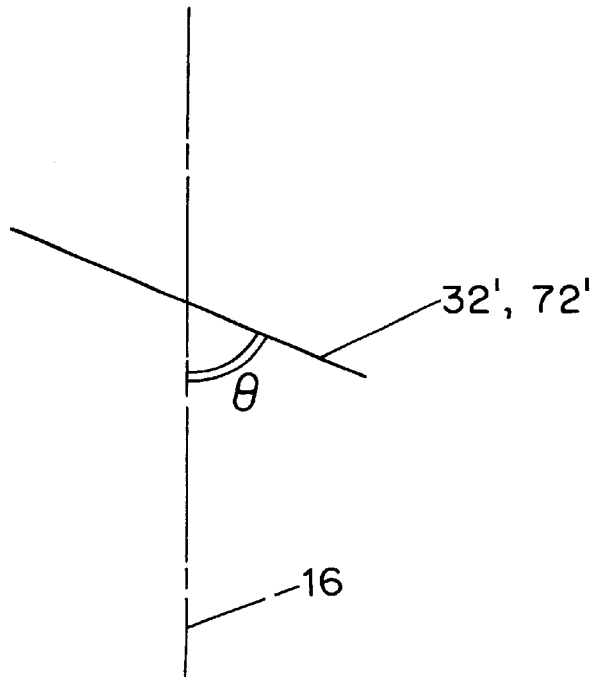
FIG. 3 shows the formation of an angle between a stent member and an axis of a graft.

FIG. 3 shows a plane (the plane of the paper) containing graft main portion axis 16 and a projection 32' of global axis 32 into that plane. As can be seen, a non-orthogonal angle θ is formed. At least substantial portions of the global axis 32 will form such a non-orthogonal angle with the graft main portion axis 16 when projected into the plane containing the graft main portion axis 16. The first stent member is selected to have material properties which will support the graft 12 when the stent is in the second, or expanded, position. The first stent member 26 can be made of an elastic element, a ductile material, or a polymer or biodegrading polymer. The elastic materials, as discussed below, can be self-expanding, while the ductile materials can be expanded, for example, by balloon catheterization. Suitable ductile materials can include, for example, stainless steel, elgiloy, or MP 36. Suitable elastic materials can include titanium, nitinol, or elgiloy. Materials suitable for both ductile and elastic applications can have their material properties adjusted by annealing, quenching, and the like, as known to those of skill in the metallurgical arts. All of the foregoing lists of materials are exemplary, and are not to be taken as limiting. Those of skill in the art will appreciate that any of a wide variety of additional materials can be employed.

As discussed above, and with reference to FIG. 3, the first stent member global axis 32 is generally defined by a straight-line curve fit to the first stent member local axis, defined by centroids 28, in a coordinate system substantially coincident with the generally tubular graft main portion 14. Further, at least substantial portions of the first stent member global axis 32 form a non-orthogonal angle, such as, for example, angle θ, with the graft main portion axis 16 when they are projected into a plane containing the graft main portion axis 16. It will be appreciated that angle θ need not be uniform; for example, in some places, the global axis 32 may define an orthogonal angle, but in general, it would be desirable for it to be nonorthogonal. In some embodiments, as shown in FIG. 1, the global axis 32 generally forms a helix. It will be understood that, when projected into a plane, the stent member global axis does not necessarily form a straight line, but a tangent to the projection 32' can be used to define the non-orthogonal angle. The mathematics of helical, and other functions which are not plane curves is well-known, and can be found, for example, in the book *Advanced Engineering Mathematics* by Erwin Kreyszig, such as at pages 374–75 of the 4th Edition published by John Wiley & Sons, Inc. in 1979.

First stent member 26 is integrally secured to textile graft 12 by the at least one graft yarn of which the graft 12 is formed. As set forth above, graft 12 is shown as a plain-weave woven graft for illustrative purposes.

Figure 4A:
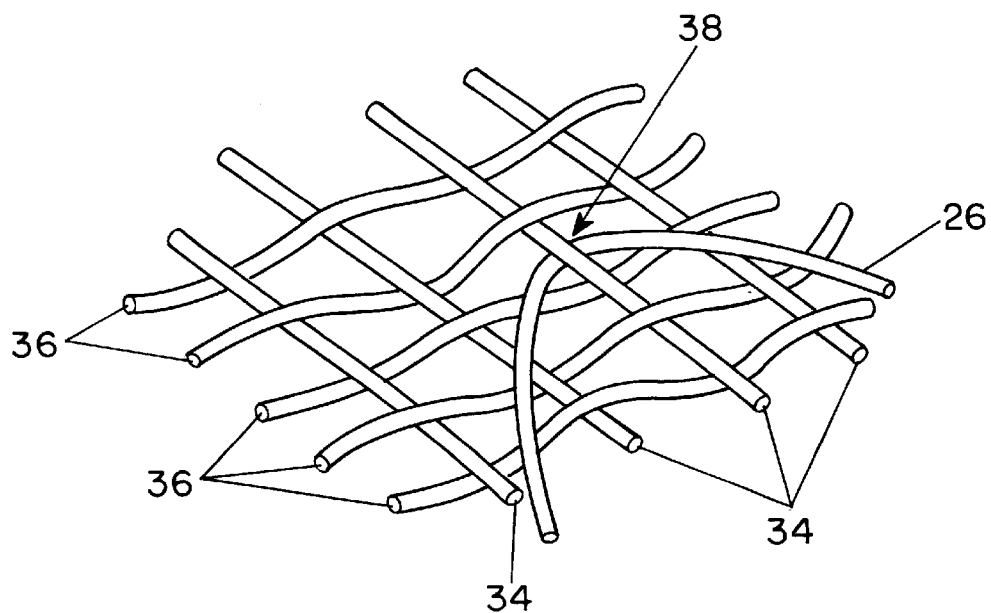
FIG. 4A shows one method of securing a stent member.
Figure 4B:
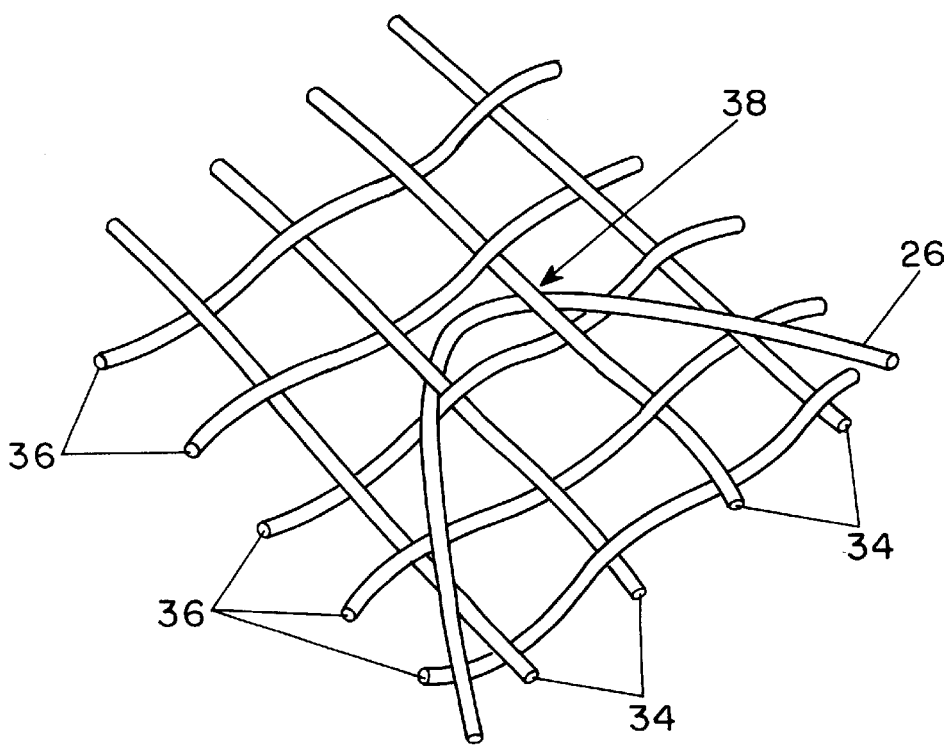
FIG. 4B shows another method of securing a stent member.
Figure 4C:
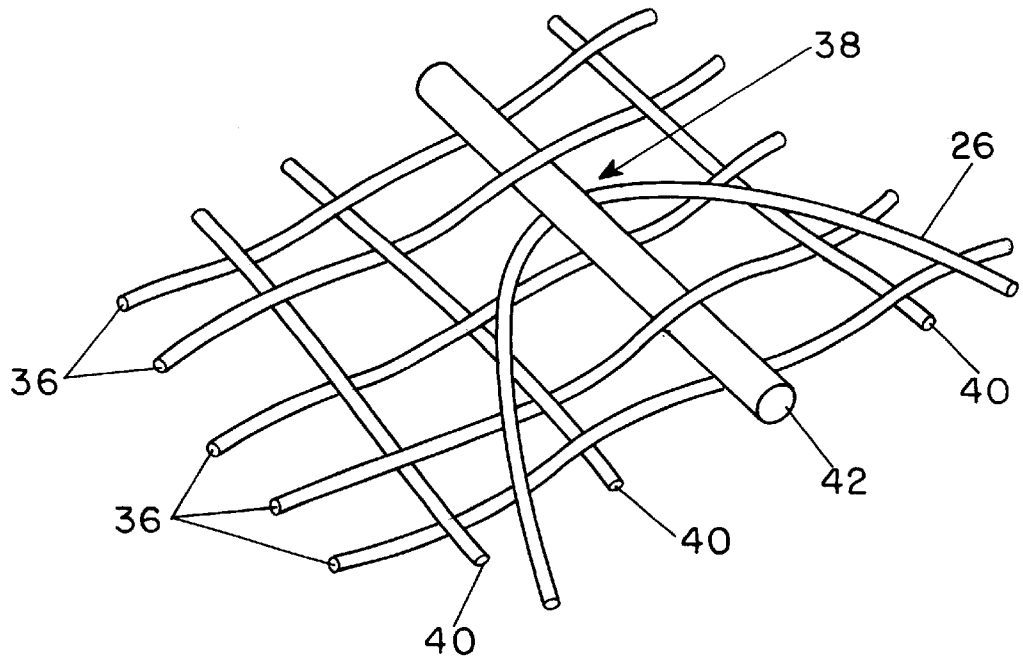
FIG. 4C shows yet another method of securing a stent member.

Reference should now be had to FIGS. 4A, 4B and 4C. As noted, textile graft 12 can be woven, and can be any kind of weave, including, for example, a plain weave, a herringbone weave, a satin weave, a basket weave, and the like. With reference to FIG. 4A, a portion of graft 12 is shown as a plain-weave including a plurality of warp yarns 34 and a plurality of fill or weft yarns 36. Fill yarns 36 are substantially orthogonal to warp yarns 34. The at least one graft yarn which integrally secures the first stent member 26 can be at least one of the plurality of warp yarns 34 and the plurality of fill yarns 36. In one embodiment, the stent member 26 is secured by at least one of the plurality of warp yarns 34 at an interweave point 38. At present, it is believed that weaving with a jacquard head would be desirable when weaving tubes, in order to obtain warp yarn control to interweave at any point around the diameter of the tube.

With reference now to FIG. 4B, if desired, first stent member 26 can be secured by at least two of the warp yarns 34 at each interweave point 38.

With reference to FIG. 4C, the plurality of warp yarns 34 can, if desired, be divided into a first group of warp yarns 40 and a second group of warp yarns 42. Only a single member of the second group 42 as shown in FIG. 4C, for exemplary purposes. The first group of warp yarns 40 would generally not be employed at the interweave points 38 and would be selected for desired properties of the underlying graft 12. The second group of warp yarns 42 would be employed at the interweave points 38 and could be selected for desirable properties in securing the first stent member 26. It will be appreciated that desirable properties for the underlying graft would include control of porosity, strength, and flexibility. Thus, suitable materials for the first group of warp yarns 40 would include (but not be limited to) polyester, PTFE, polyglycolic acid (biodegradable applications), and the like. Similar comments apply to the fill yarns. Furthermore, desirable properties for the second group of warp yarns used for securing the stent member 26 would include high strength, sealing ability, flexibility, and abrasion resistance. Thus, yarns 42 could have a larger denier than yarns 40, could be composite yarns, could be textured yarns, or could be made of a stronger material. At present, materials such as polyester, PTFE, and the like are believed preferable for yarns 42.

Figure 4D:
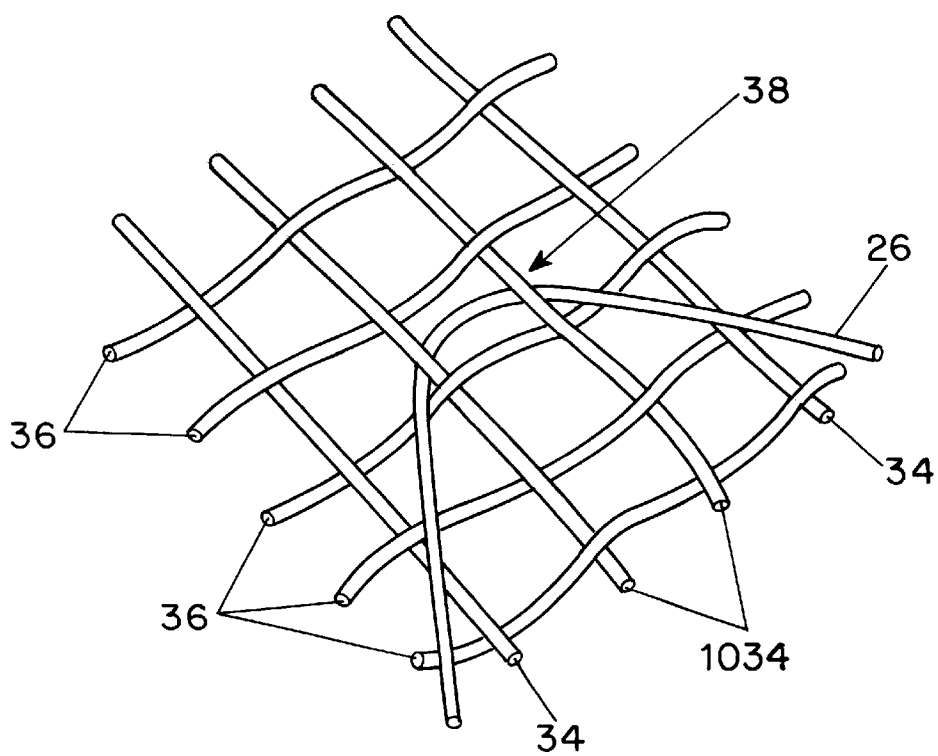
FIG. 4D is a view similar to FIG. 4B with texturized stent-securing yarns.

Textured yarns can be used for any of the warp yarns and/or the fill yarns discussed throughout this application, to enhance fluid integrity at the interweave points. FIG. 4D shows a view similar to FIG. 4B wherein the yarns designated as 1034 are textured or texturized, to enhance fluid integrity. "Textured" and "texturized" are used interchangeably in this application and should be given their ordinary meaning in the textile arts. One or more texturized yarns 1034 can be employed; two are shown in FIG. 4D. Bands of fill yarns adjacent the interweave points could also be texturized. Any of the yarns of the present invention can have thicknesses ranging from about 0.0005 inches (about 0.013 mm) to about 0.030 inches (about 0.76 mm), although this range is not limiting. Expressed in terms of Denier, yarns for medical applications can range, for example, from about 10 Denier to about 80 Denier, although this range should not be taken as limiting. Non-medical applications, such as industrial filtration and abrasive cloths, can use any desired Denier, for example, up to 1200 Denier or higher. So-called microdenier yarns can be employed, wherein the yarns have a number of filaments greater than the Denier of the yarn. For example, a 50 Denier microdenier yarn could have 68 filaments. Microdenier yarns can be employed to enhance strength and reduce porosity such yarns tend to flatten out and thus reduce porosity. Microdenier yarns can be employed for any of the yarns of the present invention.

Note that graft main portion 14 is shown as having a slight curve in FIG. 1. This is for purposes of illustration, to show the flexibility of the structure. It will be appreciated that the structure can be substantially straightened out such that axis 16 would describe a substantially straight line. This is depicted in FIG. 3.

Referring back to FIGS. 1&3, it will be appreciated that the first stent member local axis, defined by the centroids 28, defines a plurality of undulations 44 which extend on first and second sides of the first stent member global axis 32. Any desirable shape can be used for undulations 44. They are shown in FIG. 1 as being substantially sinusoidal. Thus, they can be periodic, but need not be. Furthermore, in addition to sinusoids, so-called "zig-zag" shapes, with a substantially triangular profile and suitable rounding at the apexes can be employed. Other types of shapes are known in the art, and are set forth, for example, in U.S. Pat. No. 5,556,414 to Turi and U.S. Pat. No. 5,575,816 to Rudnick et al., the disclosures of both of which are expressly incorporated herein by reference. It will be appreciated that periodic undulations 44 are substantially periodic about the global axis 32 of the first stent member 26.

As noted above, substantial portions of the first stent member global axis 32, in the embodiment being discussed, form a non-orthogonal angle with the graft main portion axis 16 when projected into a plane containing the axis 16. When the textile graft 12 is a woven graft, it will appreciated that it would normally comprise a plurality of warp yarns 22 and a plurality of weft yarns 24 which would be substantially orthogonal to the warp yarns 22. In this case, the first stent member global axis 32 would be substantially non-orthogonal to both the plurality of warp yarns 22 and the plurality of weft or fill yarns 24, as shown in FIG. 1.

The non-orthogonal angle θ which the first stent member global axis 32 forms with the graft main portion axis 16 can be a helix angle which is selected to permit the first stent member 26 to extend substantially between the first and second graft main portion ends 18, 20 and to obtain substantially homogeneous compressive and flexural properties for the combined stent/graft structure 10. It is presently believed that any non-orthogonal helix angle is operative to achieve these goals, with a range of about 10 degrees to about 85 degrees being preferred, and a range of about 45 degrees to about 85 degrees being somewhat more preferred. A value of about 82 degrees is presently believed to be most preferable. As discussed below, the present invention can include embodiments where the angle θ is 90 degrees, that is, orthogonal, in some or even all locations.

As noted above, the first stent member 26 is generally wire-shaped. It can have a circular cross-section, as shown in FIG. 2, or can be elliptical, oblong, or any other desired shape. Diameters of stent and structural members discussed herein can range from about 0.003 inches (about 0.08 mm) to about 0.035 inches (about 0.9 mm) for medical applications, although these values should not be taken as limiting. Thicknesses as large as the order of 0.1 inch (2.5 mm) or more are contemplated for industrial fabric applications. In one embodiment the stent member 26 is a wire formed from a ductile material which undergoes plastic deformation induced by a separate expanding force in expanding from the first position to the second position. The separate expanding force can come from balloon catheterization, for example, as discussed below. If desired, first stent member 26 can be formed from a wire made from an elastic material which undergoes substantially elastic deformation in expanding from the first position to the second position. In this case, the first stent member 26 can expand from the first position to the second position at least substantially by stored energy which is released upon removal of an external constraint, such as a sheath, again as discussed below. Suitable materials for both the elastic and ductile cases have been discussed above.

Figure 5:
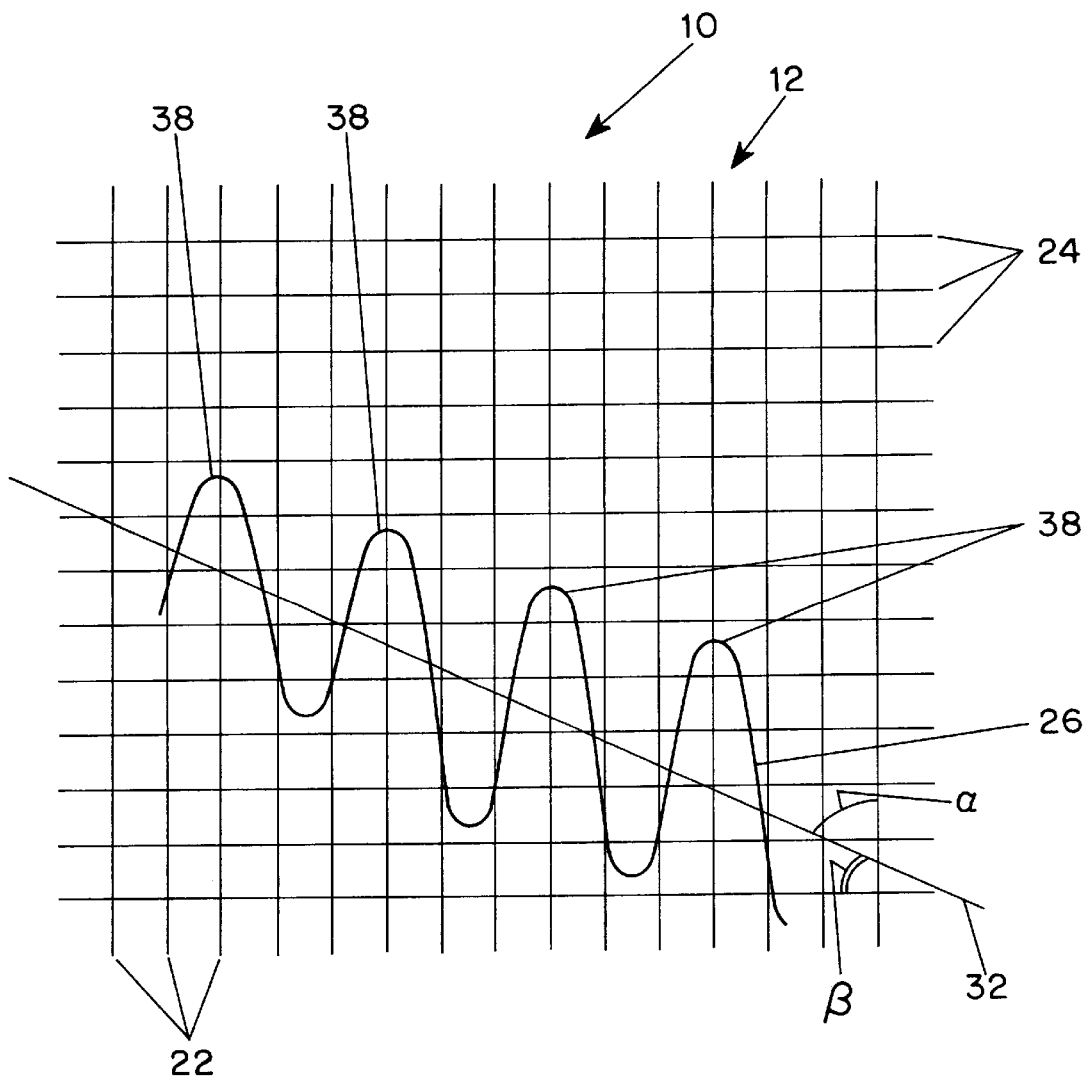
FIG. 5 shows interweaving of a stent member with a woven graft portion.

Referring now to FIG. 5, which shows the stent/graft structure 10 "unfolded" into a flat plane for convenience in illustration, the first stent member 26 can be secured to the graft portion 12 at a plurality of interweave points 38. Stent member 26 can be secured by at least one warp yarn 22 at each of the interweave points 38, and adjacent interweave points can be separated by a predetermined number of fill yarns 24 and a predetermined number of warp yarns 22. For illustrative purposes, in FIG. 5, each interweave point 38 is separated by two warp yarns 22 and by one fill yarn 24. Any desired number can be used; the example of FIG. 5 is solely for illustrative purposes. It will be appreciated that, for any given shape of stent member 26, the predetermined number of warp yarns and predetermined number of fill yarns together define a substantially non-orthogonal angle α which the first stent member global axis 32 forms with the plurality of warp yarns 22 and a complimentary substantially non-orthogonal angle β=90°−α which the first stent member global axis 32 forms with the plurality of fill yarns 24.

In another form of the present invention, the stent member can be provided with a plurality of securing portions which are positioned substantially parallel to the warp yarns and the stent member can be integrally secured to the graft, at a plurality of interweave points, by one or more weft yarns engaging a respective one of the securing portions. Further details will be provided with respect to the discussion of FIGS. 23A–23G below.

As noted, the present invention can be used to repair a body tube, of any type, in a living body. One application which is believe to be especially promising is for the repair of an abdominal aortic aneurysm in a human being. As is well-known, the human aortic artery bifurcates in the abdominal region. Accordingly, to repair aneurysms in this area, it is desirable to employ a bifurcated stent/graft structure.

Figure 6:
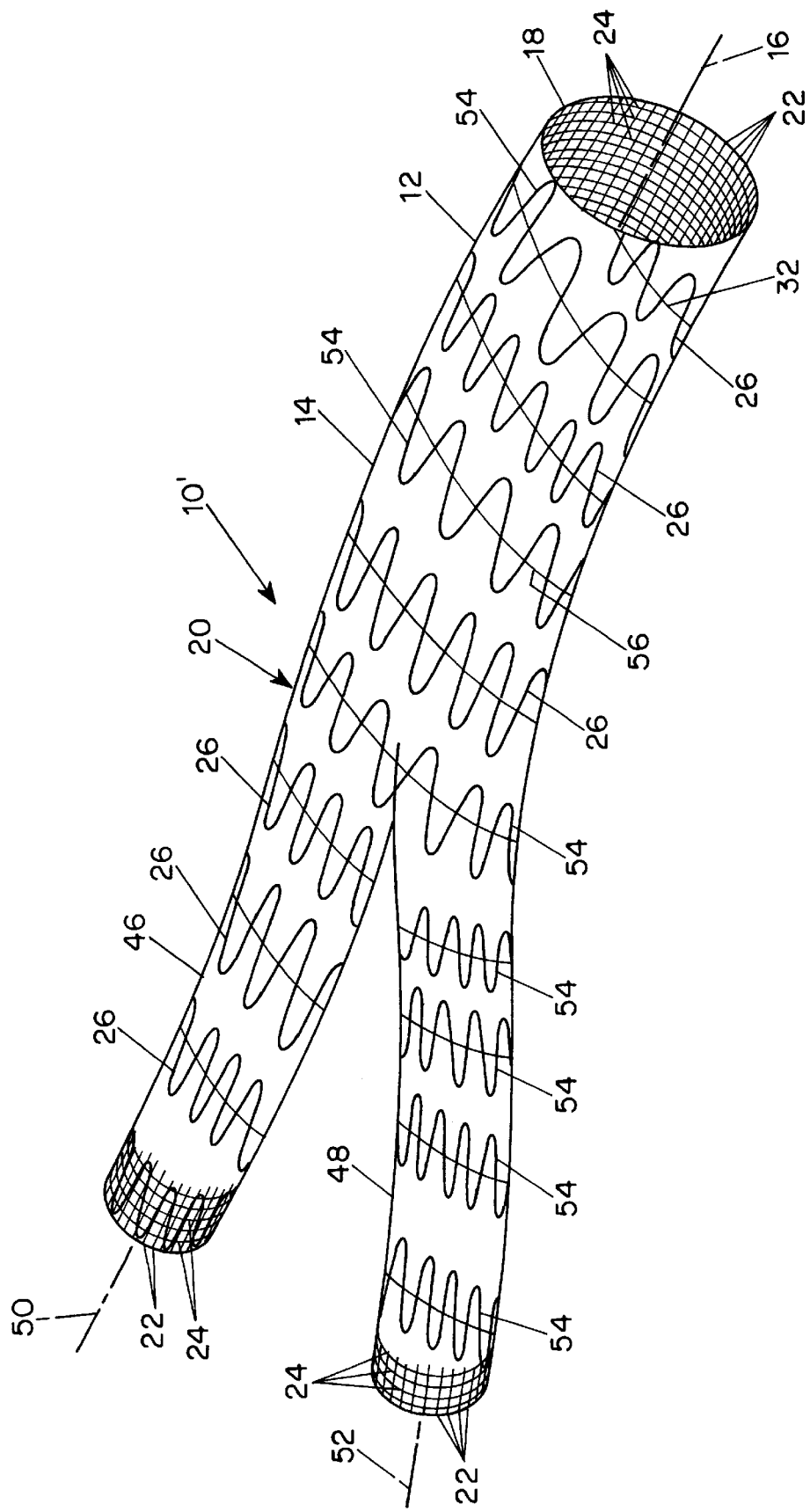
FIG. 6 shows a first type of bifurcated stent/graft structure.

Reference should now be had to FIG. 6, which depicts a bifurcated embodiment of the present invention, designated generally as 10'. Items in FIG. 6 which are similar to those in the preceding figures have received the same reference character. Structure 10' includes a bifurcated textile graft portion. The textile graft portion includes the graft main portion 14 as before, and first and second secondary portions 46, 48 respectively emanating from the second graft main portion end 20. First and second secondary portions 46, 48 extend from the second graft main portion end 20 in a substantially fluid-integrity-enhancing fashion. By this, it is meant that the overall structure enhances the fluid integrity of the bifurcated body tube, such as the aorta, into which the structure is to be placed. Those of skill in the art will appreciate that this can be achieved by having a substantially fluid-tight graft portion, or by having a graft portion which is not fluid tight in and of itself, but which "grows into" the surrounding body tubes such as to enhance the fluid integrity of the tubes. First and second secondary portions 46, 48 are each generally tubular and have first and second secondary portion axes 50, 52 respectively. The first secondary portion is formed, at least in part, by at least one first secondary portion yarn and the second secondary portion 48 is formed, at least in part, by at least one second secondary portion yarn. For illustrative purposes, FIG. 6 shows both secondary portions 46, 48 as being plain-weave portions similar to the main portion 14, each having a plurality of warp yarns 22 and a plurality of weft or fill yarns 24.

The stent of structure 10' further comprises a second elongate wire-shaped stent member 54. Second elongate wire-shaped stent member 54 has both a second stent member global axis and a second stent member local axis, defined in entirely the same fashion as for the first stent member 26 discussed above. The second stent member 54 is also integrally secured to the graft by at least one graft yarn of which the graft is formed. This can be accomplished as discussed above, for the exemplary case of a plain-weave. Substantial portions of the second stent member global axis, which has been designated 56, form a non-orthogonal angle with the graft main portion axis 16 when projected into a plane containing the graft main portion axis 16, as discussed above with respect to the first stent member. The second stent member 54 has material properties which are preselected to support the graft when in the second position, and the local axis of the second stent member is generally defined by the centroids 28 of adjacent cross-sections of the second stent member, just as shown in FIG. 2 for the first stent member 26. The second stent member global axis 56 is generally defined by a straight-line curve fit to the second stent member local axis in a coordinate system which is substantially coincident with the generally tubular graft main portion 14, again, as set forth above with respect to the first stent member 26.

Still with reference to FIG. 6, it will be seen that both the first and second stent members 26, 54 are present in the graft main portion 14. The first stent member 26 is integrally secured to the first secondary portion 46 by at least one first secondary portion yarn. Substantial portions of the first stent member global axis 32 form a non-orthogonal angle with the first secondary portion axis 46 when projected into a plane containing the first secondary portion axis 46. Again, this is similar to the description with respect to the tubular graft main portion 14 set forth above.

Similarly, the second stent member 54 is integrally secured to the second secondary portion 48 by the at least one second secondary portion yarn, with substantial portions of the second stent member global axis 56 forming a non-orthogonal angle with the second secondary portion axis 48 when projected into a plane containing the second secondary portion axis 48. As shown in FIG. 6, the first and second stent members 26, 54 can be axially spaced in the graft main portion 14 and can form a substantially double helical structure therein.

Figure 7:
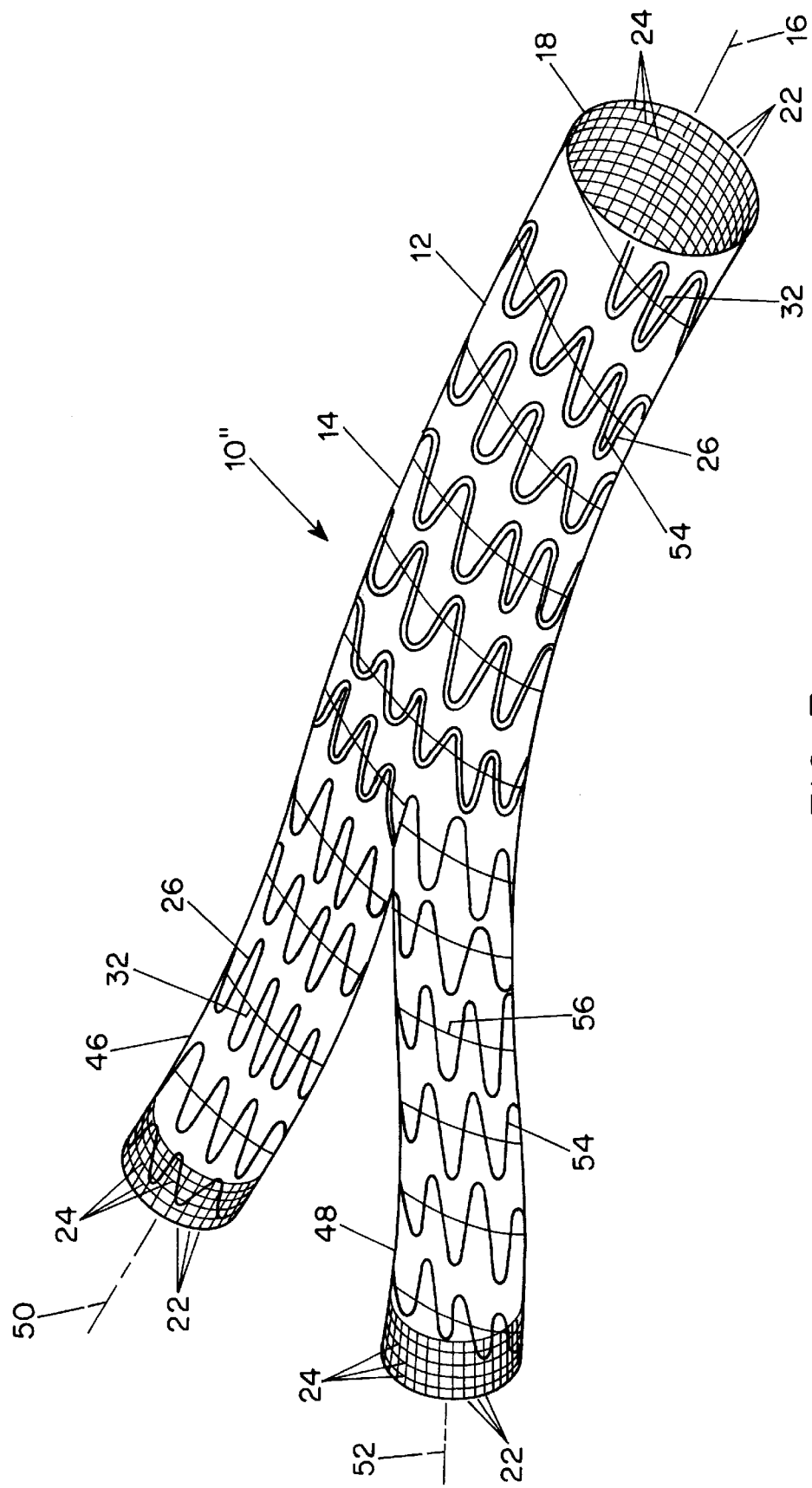
FIG. 7 shows another type of bifurcated stent/graft structure.

Reference should now be had to FIG. 7, which depicts an alternative embodiment of bifurcated stent/graft structure, designated generally as 10". Construction of this embodiment is essentially similar to that of embodiment 10', except that the first and second stent members 26, 54 are substantially co-extensive in the graft main portion 14. Accordingly, only the first stent member global axis 32 has been shown in the main portion 14, since it would normally be substantially coincident with the global axis 56 of the second stent member 54. It is to be understood that by "coincident" or "co-extensive", it is meant that the first and second stent members 26, 54 would be very close to each other or touching.

With reference back to FIG. 1, it will be appreciated that the first stent member 26 can extend substantially from the first graft main portion end 18 to the second graft main portion end 20. When the stent member global axis 32 is non-orthogonal to the axis 16 of generally tubular graft main portion 14, the desired extension between the first and second ends 18, 20 can be achieved with a single stent member, without the need to put multiple stent members in at a plurality of locations along the axis 16. This can enhance reliability, simplify manufacturing, and provide support along the entire length of the stent/graft structure. Uniformity of structural and flexural properties (e.g., flexural rigidity) throughout the structure can be achieved. Furthermore, it can provide radiopacity such that the stent/graft structure can be viewed on a fluoroscope, with x-ray equipment, and the like.

Throughout the foregoing, main portion 14, first secondary portion 46 and second secondary portion 48 have been depicted as having a substantially constant diameter, with the diameter of the secondary portions 46, 48 being somewhat less than that of the main portion 14. It will be appreciated that any of the portions can be formed in a tapered fashion, if desired.

Figure 8:
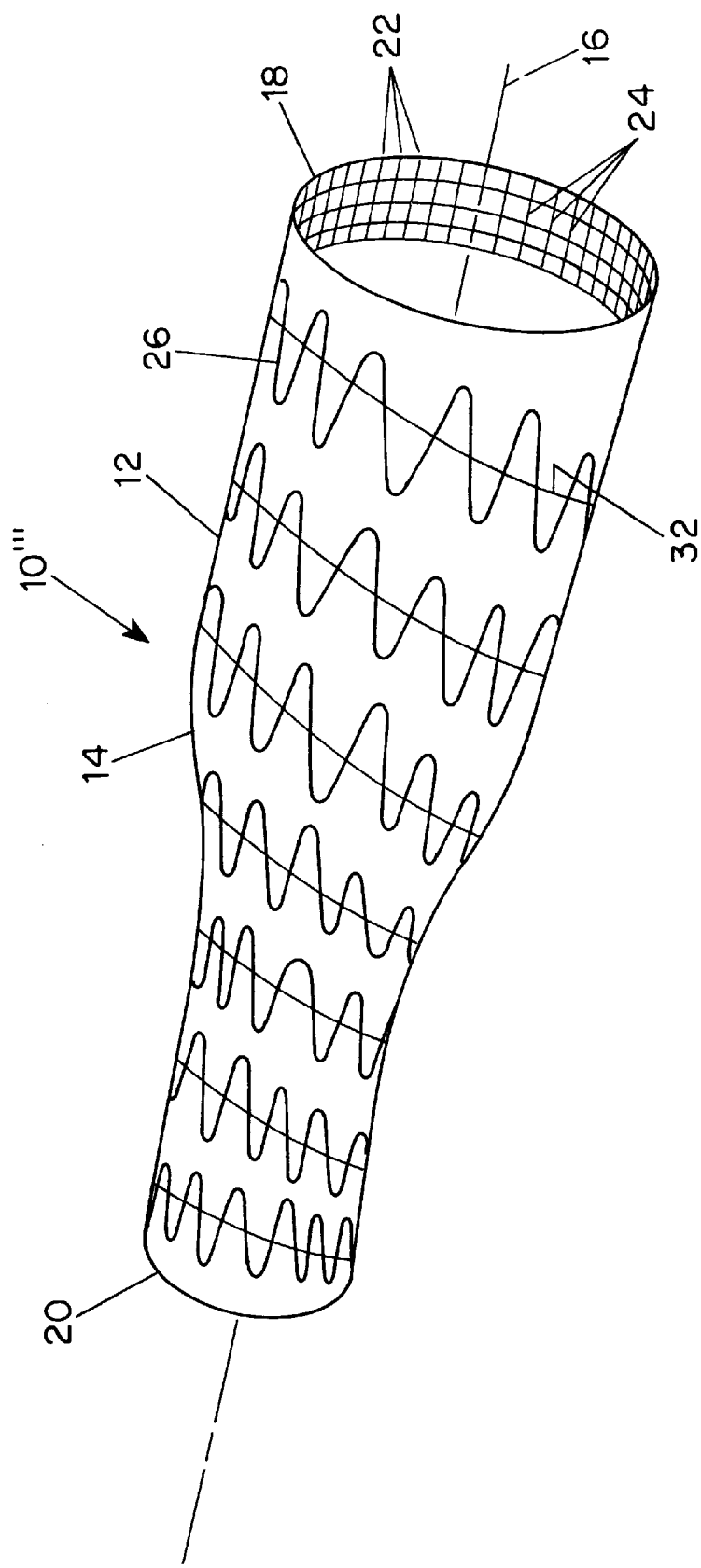
FIG. 8 shows a tapered stent/graft structure.

Reference should now be had to FIG. 8, which shows an embodiment of the invention 10''', substantially similarly to that depicted in FIG. 1, except wherein the graft main portion 14 tapers from the first graft main portion end 18, to the second graft main portion end 20. The taper in FIG. 8 is not "straight," but is more rapidly tapered in the middle of the main portion 14.

Figure 9:
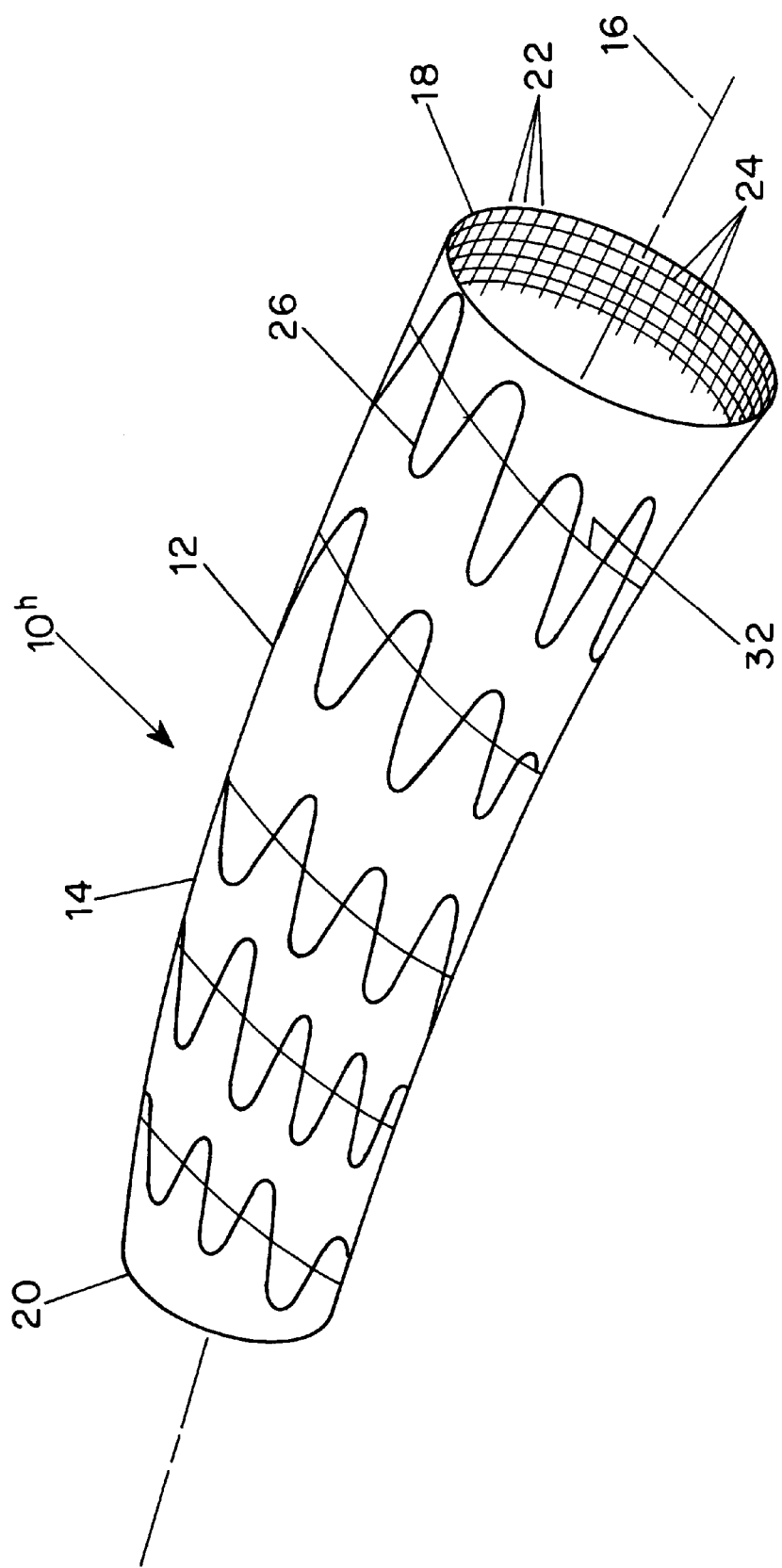
FIG. 9 shows another type of tapered stent/graft structure.

Referring now to FIG. 9, an alternative tapered embodiment of the invention is depicted, designated as $10^{iv}$. In this case, the graft main portion 14 also tapers from the first end 18 to the second end 20, but in a more regular or "straight taper" fashion.

Figure 10:
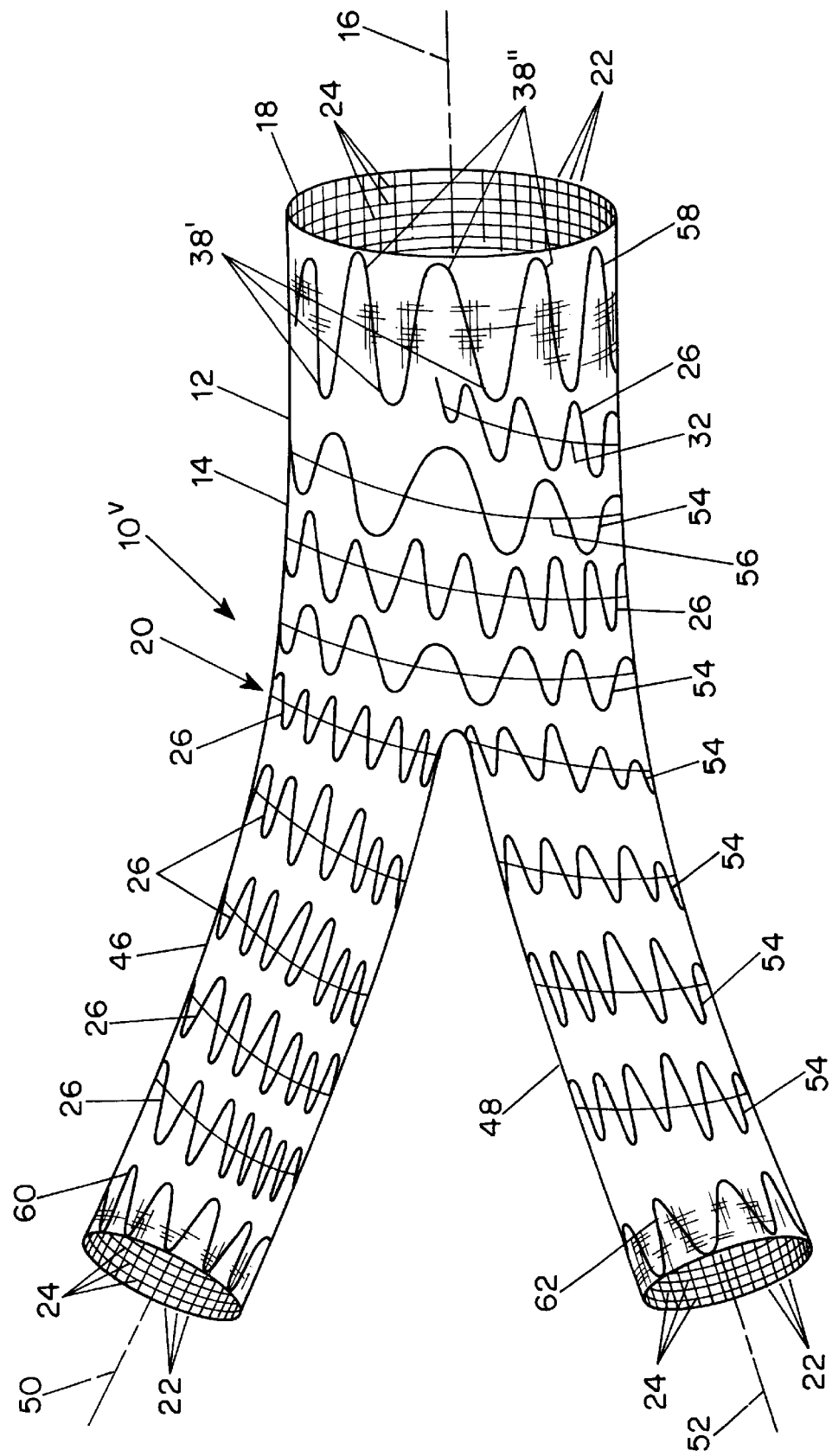
FIG. 10 shows another bifurcated stent/graft structure with a composite stent.

Reference should now be had to FIG. 10, which depicts a composite stent/graft structure, designated generally as $10^{v}$, in accordance with the present invention. The structure $10^{v}$, is essentially similar to the structure depicted in FIG. 6. The first stent member 26 can be formed of an elastic material, as set forth above, and can be selected for flexible self-support of the graft main portion 14. The first stent member 26 can extend along the graft main portion 14 but can terminate before reaching at least one of the first and second graft main portion ends 18, 20. As shown in FIG. 10, for illustrative purposes, first stent member 26 terminates before reaching first end 18 of graft main portion 14.

Structure $10^{v}$ further includes at least a third stent member 58, and can preferably include a fourth stent member 60 and a fifth stent member 62. The third stent member 58 can be formed of a ductile material selected for apposition of the body tube inner surface by balloon expansion. The third stent member 58 can be located at the at least one of the first and second graft main portion ends 18, 20 which the first stent member 26 terminates before reaching. In FIG. 10, this is the first end 18, for illustrative purposes. The third stent member 58 can be integrally secured to the graft by at least one graft yarn of which the graft is formed; for example, it can be secured at a plurality of interweave points 38 as set forth above. Since stent members 58, 60, 62 are preferably selected to be formed of ductile material for apposition of the body tube inner surface, they need not necessarily extend the entire length of the structure $10^{v}$; they can be localized at the ends. Thus, members 60, 62 are located at the ends respectively of the first and second secondary portions 46, 48. Since these stent members 58, 60, 62 need not extend the entire length of the structure, they can have a global axis which is orthogonal to the respective axes 16, 50, 52. They can be secured, for example, as shown in FIG. 5 but, for example, without any fill yarns 24 between adjacent interweave points 38. It will be appreciated that stent members such as 58, 60, 62 can be used in any of the embodiments of the invention, including non-bifurcated embodiments, in which case, for example, there might be only a single elastic stent member 26, in which case the third stent member 58 could be referred to as the second stent member.

In view of the foregoing discussion, it will be appreciated that, in some embodiments of the invention, the stent could simply include a first elongate wire-shaped stent member 26 having a plurality of undulations 44, wherein the global axis 32 of the first stent member 26 was substantially orthogonal to the axis 16 of the generally tubular graft main portion 14. In this case, for example, a woven graft such as graft 12 could be adapted to enhance fluid integrity of the body tube, as set forth above, and could have a generally tubular graft main portion 14 with a graft main portion axis 16 and first and second graft main portion ends 18, 20 respectively. The woven graft 12 would be formed from a plurality of warp yarns 22 and a plurality of fill yarns 24 substantially orthogonal to the plurality of warp yarns. Note that, in the general case, graft 12 could be any type of a textile graft and could include knit or braided structures; however, a woven graft is referred to in this context.

In the immediately preceding case, the stent could include a stent which was expandable between a first position permitting easy insertion of the stent into the body tube and a second position where the stent pressed securely against the inside surface of the body tube. The stent could include an elongate wire-shaped stent member with a plurality of undulations, such as, for example, stent member 58 previously depicted. This stent member could be integrally secured to the graft at a first plurality at interweave points 38' as shown in FIG. 10. As discussed above, the member could be secured by at least one warp yarn at each of the first plurality of interweave points 38'. The first plurality of interweave points could be spaced circumferentially about the graft 12 and could be separated from each other by a predetermined number of the warp yarns 22.

Just as for the embodiments discussed above, where there was a non-orthogonal angle between the stent member global axis 32 and the main portion axis 16, the warp yarns 22 can be divided into a first group of warp yarns 40 which are not employed at the interweave points 38' and a second group of warp yarns designated as 42 which are employed at the interweave points 38'. This is depicted in FIG. 4C. Again, the first group of warp yarns can be selected for desired graft properties, and the second group of warp yarns can be selected for desirable properties in securing the appropriate stent member, all as discussed above. Alternatively, stent member 58 could be secured by at least two warp yarns 34, as discussed above, and depicted in FIG. 4B, at each of the interweave points 38'.

Still referring to FIG. 10, the first plurality of interweave points 38' could have a first substantially identical axial coordinate measured with respect to axis 16, and the stent member 58 could also be secured to the graft at a second plurality of interweave points 38" having a second substantially identical axial coordinate measured with respect to axis 16. The first and second plurality of interweave points 38', 38" could be separated by a predetermined number of the fill yarns 24. Throughout the foregoing, it will be appreciated that the stent member 58, with global axis orthogonal to axis 16 (or members 60, 62 with global axes orthogonal to axes 50, 52 respectively), could be the only stent member(s) employed in the present invention, that is, the present invention is not limited to structures wherein there is at least one stent having a non-orthogonal angle between its global axis and the axis of the corresponding graft portion.

In an alternative form of the invention, also optionally with a stent member global axis substantially orthogonal to the graft main portion axis, portions of the undulations of the stent member can be substantially parallel to the warp yarns at a plurality of securing portions, and the first stent member can be integrally secured to the graft by one or more fill yarns engaging a respective one of said securing portions at a plurality of interweave points otherwise similar to those described above. Refer also to the discussion of FIGS. 23A–23G below.

Figure 11:
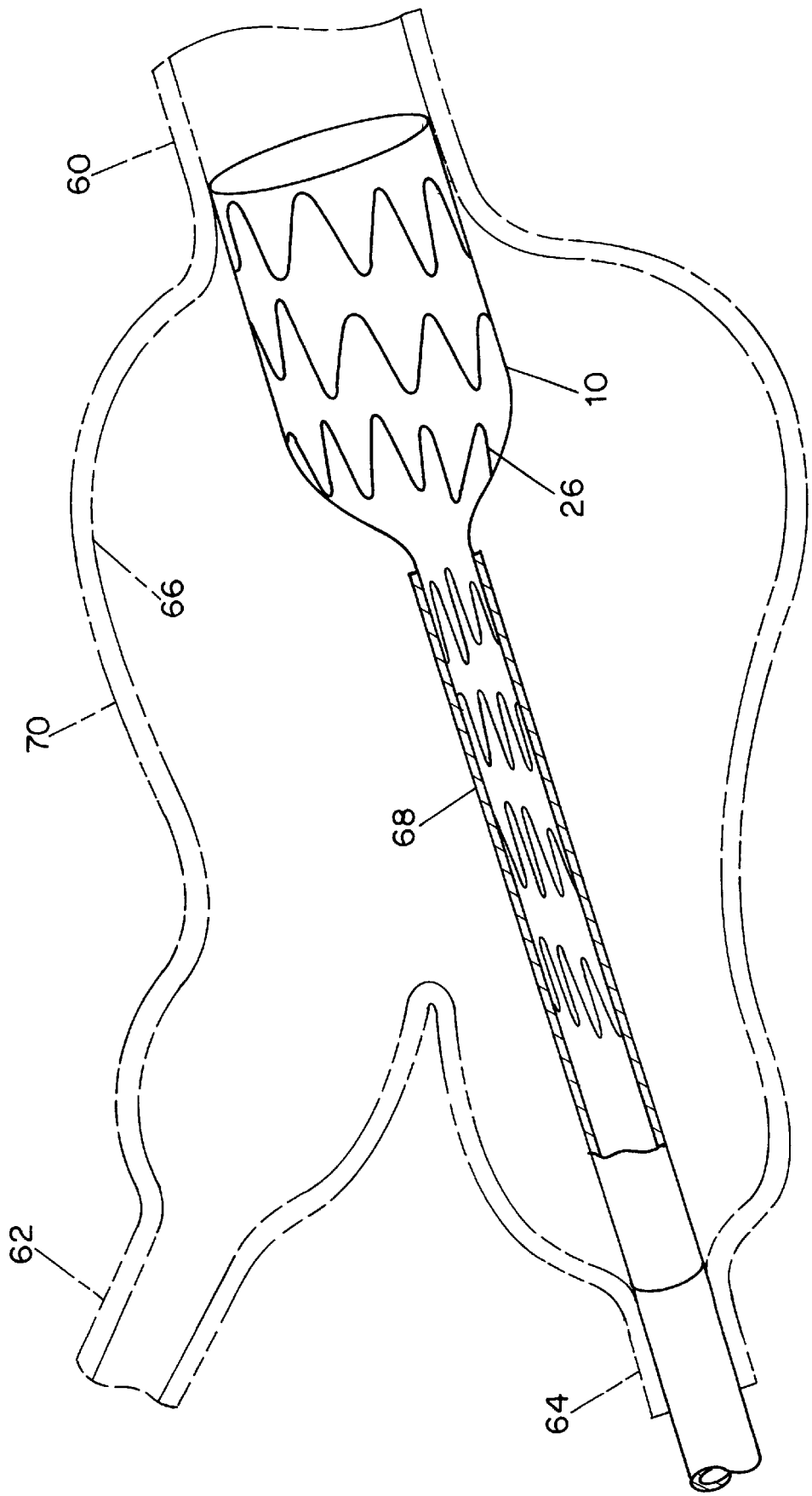
FIG. 11 shows a structure of the present invention in the process of installation into an aortic aneurysm.

Reference should now be had to FIG. 11, which depicts a self-expanding stent/graft structure, according to the present invention, being emplaced in a body tube. For illustrative purposes, FIG. 11 shows a human aorta 60 with first and second bifurcations 62, 64 and an inner surface 66. Stent/graft structure 10 includes a wire-shaped stent member 26 which is elastic in character and which will expand upon removal of an external constraint. As shown in FIG. 11, the external constraint can be provided by a tube 68. The stent is in the first position, permitting easy insertion of the stent into the body tube (such as aorta 60), when it is constrained within tube 68. The stent is in the second position, pressing securely against the inside surface 66 of the body tube 60 in the expanded region when it has emerged from the constraint of tube 68. It will be appreciated that the aorta 60 depicted in FIG. 11 has an aneurysm 70. Surgical techniques for implanting self-expanding stent devices are well known in the art, for example, as shown in U.S. Pat. No. 5,556,414 to Turi, the disclosure of which is expressly incorporated herein by reference.

For those cases wherein a balloon-expandable, ductile stent member is employed, there are also a number of well-known techniques for implantation, as depicted, for example, in U.S. Pat. No. 4,787,899 to Lazarus, U.S. Pat. No. 5,571,173 to Parodi, and U.S. Pat. No. 5,628,783 to Quiachon et al. The disclosures of the Lazarus '899, Parodi '173 and Quiachon et al. '783 patents are also expressly incorporated herein by reference. Thus, those of skill in the surgical arts will appreciate a number of ways in which the stent/graft structures previously disclosed herein can be implanted into a patient.

Figure 12:
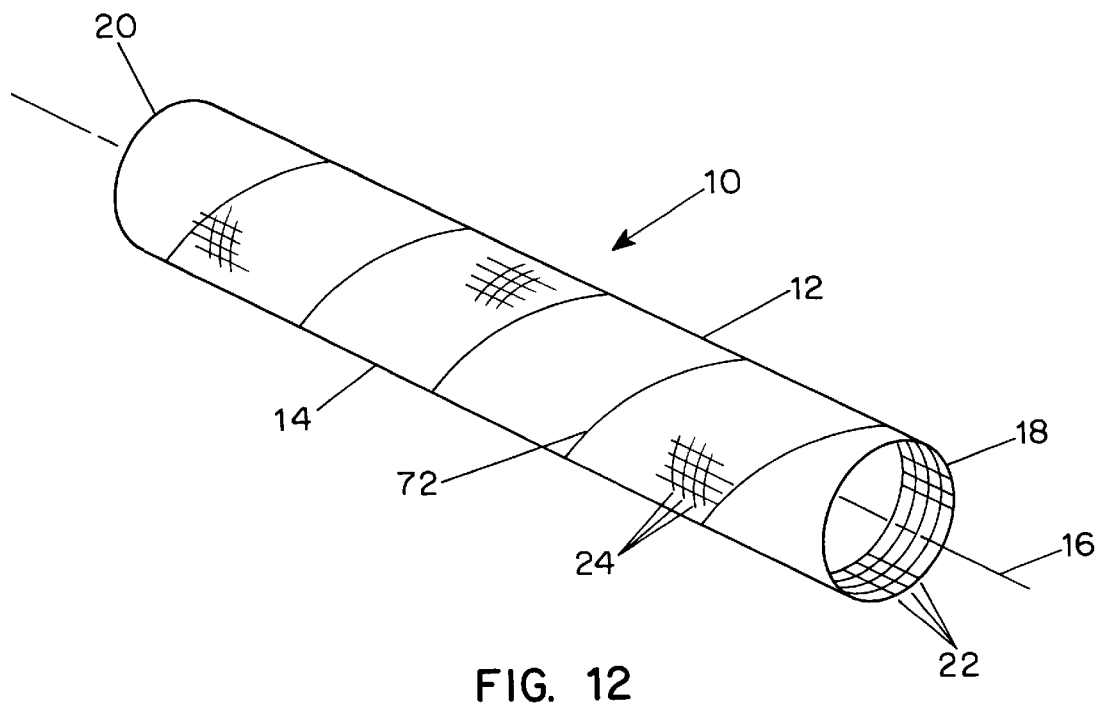
FIG. 12 shows a stent/graft assembly with a non-undulating stent member.

Reference should now be had to FIG. 12, which depicts another embodiment of the present invention, designated generally as $10^{vi}$. In this case, the first stent member 72 has a local axis and a global axis, defined as above, which are substantially coincident; that is, the first stent member is not periodic about its global axis. Once again, a non-orthogonal angle is formed between the global axis of the first stent member 72 (substantially coincident with the member itself as shown in FIG. 12) and the axis 16 of the generally tubular graft main portion 14. The non-orthogonal angle which can be seen in FIG. 3, wherein 72' represents the projection of the non-periodic stent member 72 into the plane of the axis 16, can be a helix angle which is selected to permit the stent member 72 to extend substantially between the first and second graft main portion ends 18, 20 and to obtain substantially homogenous compressive and flexural properties for the combined stent/graft structure 10I. As above, almost any non-orthogonal helix angle should permit attainment of these desired features; a range of about 10 degrees to about 85 degrees is believed to be preferable, with a range of about 45 degrees to about 85 degrees believed to be somewhat more preferable. A value of about 82 degrees is presently believed to be most preferable.

It will be appreciated that, throughout the present application, the stent member is shown on the outside of the graft portion. This location is believed preferable for manufacturing purposes, but other appropriate locations are within the scope of the invention.

Figure 13A:
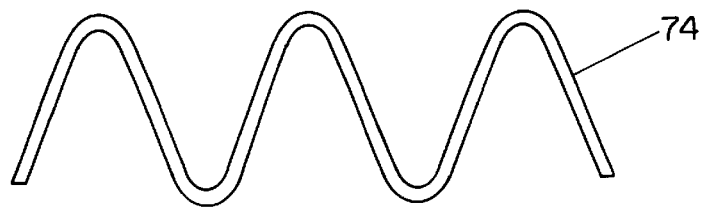
FIG. 13A and FIG. 13B show steps in forming a shape-memory structural member.
Figure 13B:
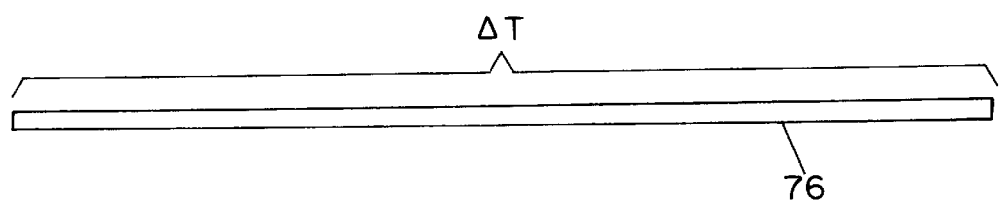

The present invention also provides a method of forming a textile with an undulating wire member therein. Referring now to FIG. 13A, an initial step includes forming a wire exhibiting shape memory behavior into an undulating wire member 74. Any suitable shape memory alloy can be used, such as nickel titanium (NiTi) and the like. Suitable shape memory allies are known in the metallurgical arts, and are discussed, for example, in U.S. Pat. No. 4,899,543 to Romanelli et al., the disclosure of which is expressly incorporated herein by reference. An additional step in the method includes training the wire to remember its shape while it is formed into the undulating wire member 74. Methods of training shape memory alloys are know in the metallurgical arts, and are set forth, for example, in the Romanelli et al patent. An additional step in the method includes causing the undulating wire member 74 to straighten by undergoing a shape-memory transformation, suggested by the notation $\Delta T$ (as in FIG. 13B), to thereby produce a straightened wire 76 with a memory of an undulating shape, as in the undulating wire member 74 of FIG. 13A. The straightened wire 76 can then be secured into a conventional textile, such as a plain-weave, using the methods discussed above, and once it is secured to the textile, it can undergo an additional shape memory transformation back to the undulating shape remembered by member 74 in FIG. 13A.

Figure 14:
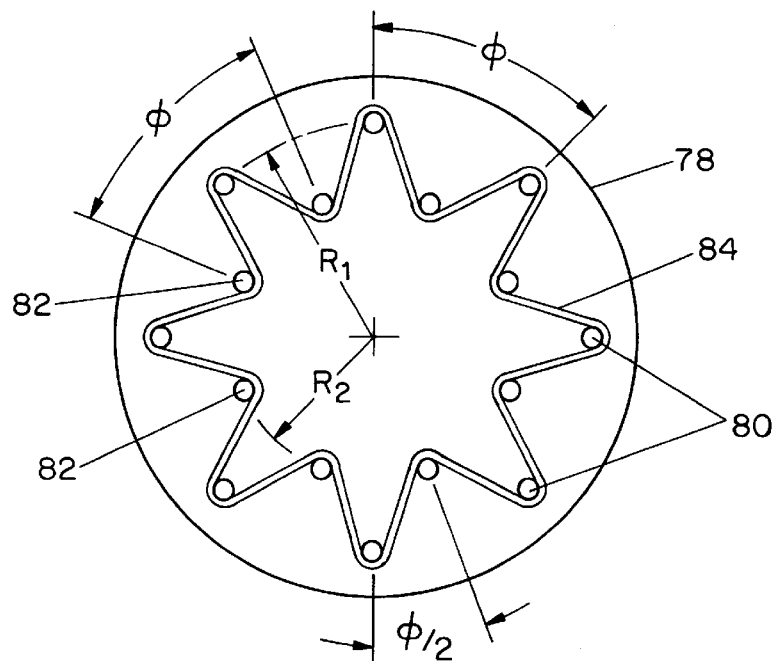
FIG. 14 depicts formation of a structural member with a first type of mandrel.

In one form of the method, the step of forming the wire into the undulating wire member 72 can include provision of a flat mandrel 78 with a first series of pins 80 spaced substantially equiangularly at a first radius $R_1$ with a spacing angle $\phi$. The flat mandrel 78 can also have a second series of pins 82, also spaced substantially equiangularly at a second radius $R_2$, also with the spacing angle $\phi$, and with the first and second series of pins being substantially $\phi/2$ out of phase, as shown in FIG. 14. In this case, the step of forming the undulating wire member can also include winding a suitable wire 84, of shape memory material, in an interlaced fashion about the pins 80, 82 to produce the undulating wire member 74. For example, the wire 84 can be wound inwardly about the outer pins 80 and outwardly about the inner pins 82, alternating inner and outer pins, as shown in FIG. 14.

Figure 15A:
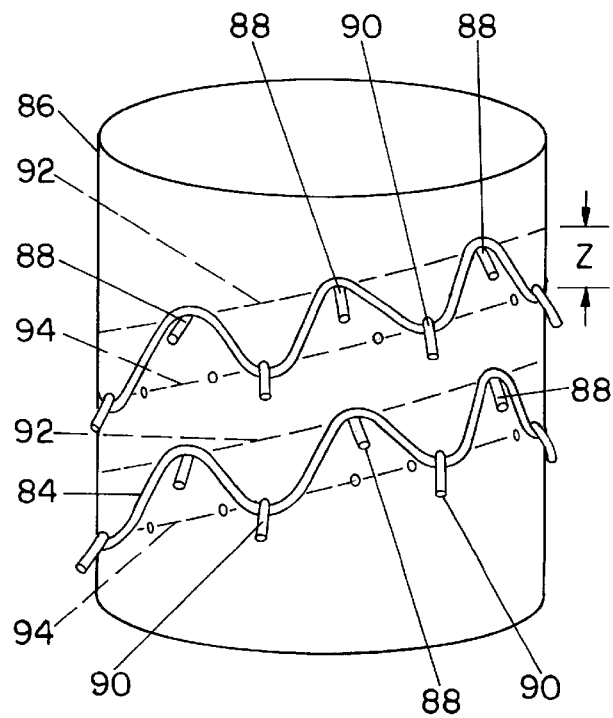
FIGS. 15A and 15B depict formation of a structural member with a second type of mandrel.
Figure 15B:
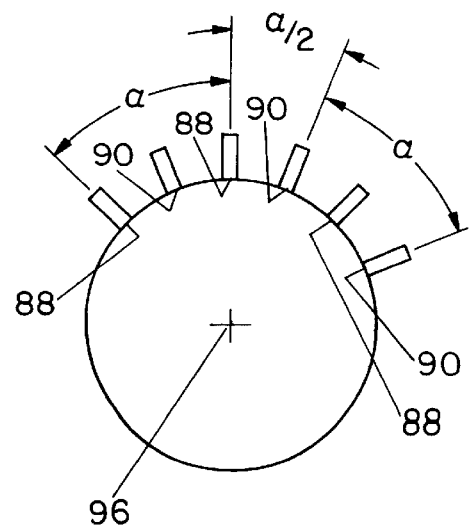

Reference should now be had to FIGS. 15A and 15B. In an alternative method, according to the present invention, of forming a textile with an undulating wire member therein, the step of forming the wire exhibiting the shape memory behavior into the undulating wire member 74 can include the sub-step of providing a cylindrical mandrel 86 with a first series of pins 88, spaced substantially equiangularly, with a spacing angle $\gamma$, along a first helical path 92. The first helical path 92 is represented by a plain dashed line. The mandrel 86 can also include a second series of pins at 90 spaced substantially equiangularly, also with the spacing angle γ, along a second helical path 94 which has a substantially identical helix angle to the first helical path 92. The second helical path 94 is represented by a dash-dotted line. The second helical path 94 can be displaced axially a predetermined distance Z from the first helical path 92. The first and second series of pins 88, 90 can be substantially γ/2 out of phase when viewed along an axis 96 of the cylindrical mandrel 86. The angular relationships are best seen in FIG. 15B. Note that FIG. 15B is drawn on a slightly smaller scale than is FIG. 15A. When the cylindrical mandrel 86 is employed, the forming step of the method can also include winding the wire 84 in an interlaced fashion about the pins 88, 90 to produce the undulating wire member 74. For example, the wire 84 can be wound generally downwardly about the first series of pins 88 and generally upwardly about the second series of pins 90, as depicted in FIG. 15A. Note that the wire 84 is not shown in FIG. 15B, for clarity.

Reference should now again be had to FIG. 5. It will be appreciated that the present invention provides a stent/graft structure. However, the textile from which the stent/graft structure is manufactured can be useful in its own right for other applications; for example, in the art of industrial filtration. Accordingly, the present invention also provides a woven textile comprising a plurality of warp yarns 22 and a plurality of fill yarns 24 which are substantially orthogonal to the plurality of warp yarns and which form a base fabric with the warp yarns. The textile also includes an elongate wire-shaped structural member (represented by wire-shaped stent member 26) which has both a structural member global axis and a structural member local axis, defined as for the stent member 26 above. In this case, the global axis for the structural member, represented by stent member 26, is defined by a straight-line curve fit to the member local axis in a coordinate system which is substantially coplanar with the warp and fill yarns 22, 24. This is true in the case when the textile is an ordinary flat textile and is not woven into a tube or the like.

The structural member, represented by stent member 26, is integrally secured to the base fabric formed from the warp and fill yarns 22, 24 at a plurality of interweave points 38. The member 26 is secured by at least one warp yarn 22 at each of the interweave points 38, and the adjacent interweave points are separated by a predetermined number of fill yarns 24 and a predetermined number of warp yarns 22, as above. The predetermined numbers of yarns determine a substantially non-orthogonal angle α between the global axis 32 of the member 26 and the warp yarns 24. Also determined is a complimentary substantially non-orthogonal angle β=90°−α, which is formed between the global axis 32 and the fill yarns 24. As shown in FIG. 5, the structural member local axis can define a plurality of undulations extending on first and second sides of the global axis 32. The undulations can be substantially periodic about the structural member global axis 32, as set forth above with respect to the stent/graft structure per se.

Any of the types of interconnection depicted in FIGS. 4A through FIG. 4C can be employed, including the provision of a first group of warp yarns which are not employed at the interweave points and which are selected for desired base fabric properties, and a second group of warp yarns employed at the interweave points and having properties selected for securing the structural member. Desirable base fabric properties can include those set forth above for the stent/graft structure, and can also include properties such as controlled porosity and fluid compatibility in industrial filtration applications. Fabric stiffness control is also important in such applications, and can be augmented with selection of a suitable structural member. Embodiments can be constructed wherein there is changing flow resistance as a function of pressure drop, as the media "bows out" and acts like a relief valve. Further, the bowing properties can be controlled with the structural member so as to vary the effective pore size to handle different particle size ranges, and the like. Greater bowing, with a less stiff structural member, will tend to stretch the textile and expand the pores. As discussed above, if desired, at least two warp yarns 22 could be employed at each of the interweave points 38, for securing the member 26.

Figure 16:
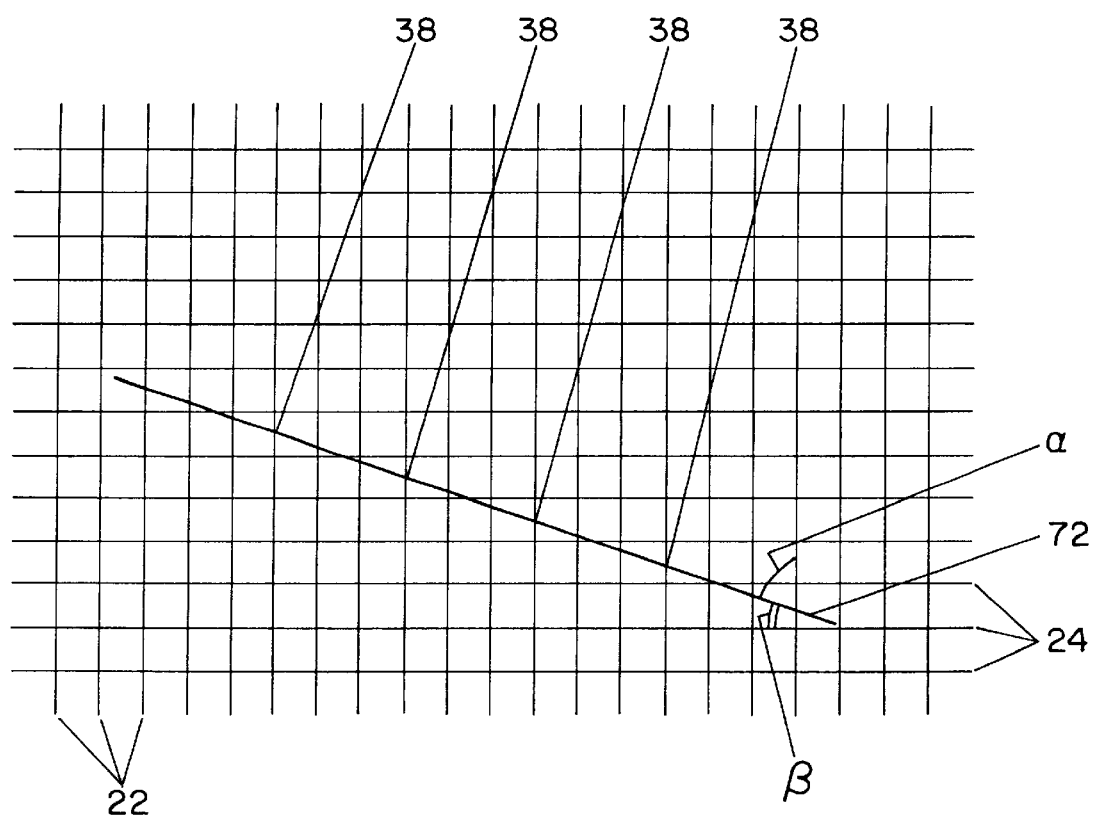
FIG. 16 shows a fabric, according to the present invention, with a nonundulating structural member therein.

Reference should now be had to FIG. 16 which shows a similar type of woven textile, but one wherein the structural member local axis and structural member global axis are substantially coincident. For example, this could represent the case of the non-undulating stent member 72, once the stent fabric was "unrolled" and laid out flat. Again, the non-orthogonal angles α and β are defined as above, and can preferably range from approximately 10 degrees to approximately 85 degrees, or more preferably from about 45 degrees to about 85 degrees. A value of about 82 degrees is presently believed to be most preferable. Again, any non-orthogonal angle can be useful, the indicated ranges are simply those presently believed to be preferred. Similar ranges are also possible for the woven textile using the undulating member, as shown in FIG. 5. Further, from a strict mathematical point of view, with reference to FIG. 16, it will be appreciated that a generally helical member when "unrolled" would not necessarily form a straight line in a plane; the comparison to "unrolling" the non-undulating stent/graft device discussed above (embodiment 10″) is not completely precise, but is employed for convenience in illustration. Still with reference to FIG. 16, it will be appreciated that the predetermined number of warp yarns between each interweave point is two and the predetermined number of fill yarns 24 between each interweave point is one; again, this is for illustrative purposes, and any desired number of warp and fill yarns can be chosen.

In another form of woven textile according to the present invention, the structural member can have a plurality of securing portions which are positioned substantially parallel to the warp yarns, and the structural member can be integrally secured to the base fabric, at a plurality of interweave points, by one or more fill yarns engaging a respective one of the securing portions. Refer also to the discussion of FIGS. 23A–23G below.

Figure 17A:
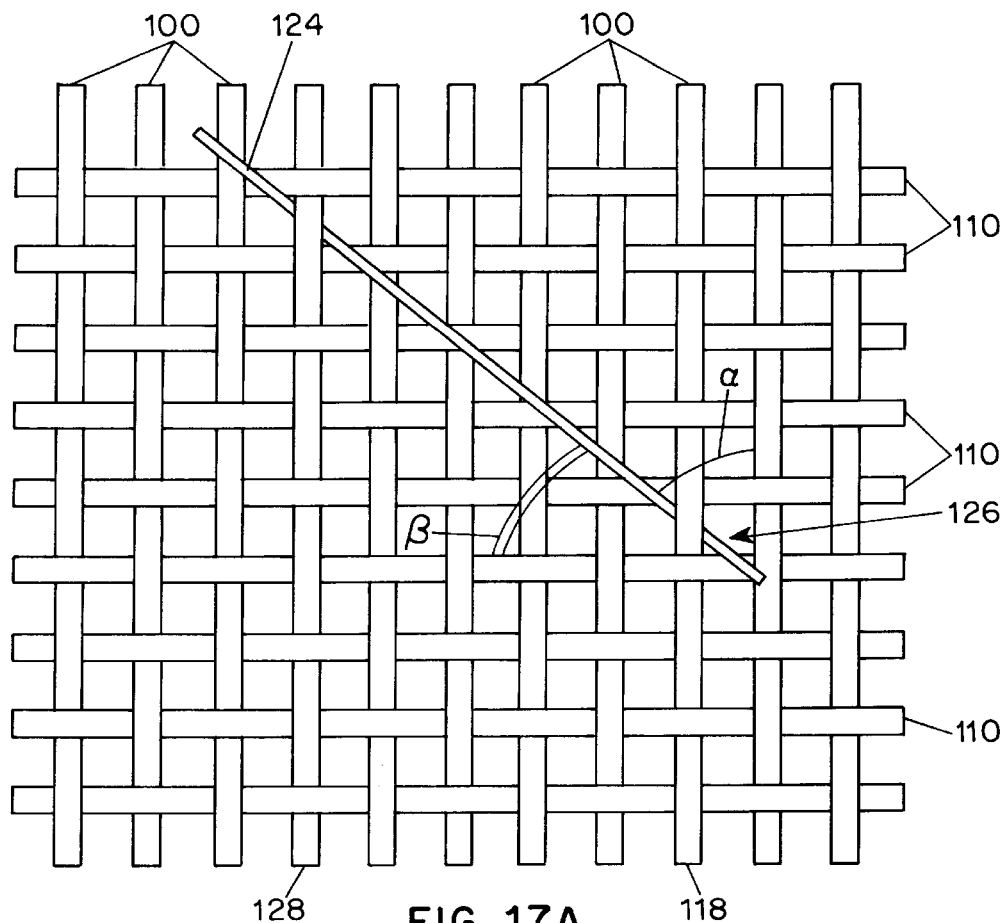
FIGS. 17A–17I show various steps in a manufacturing method according to the present invention.
Figure 17B:
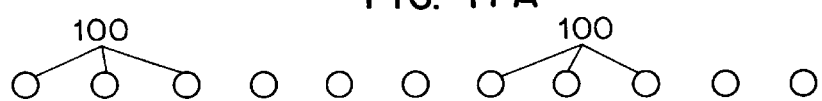
Figure 17C:
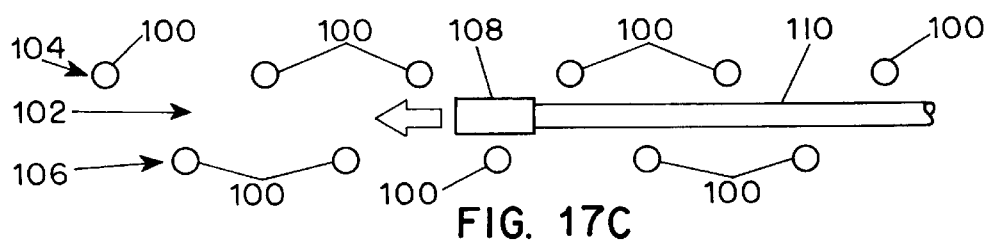

Reference should now be had to FIGS. 17A–17G which depict a method of manufacturing a woven textile having a structural member integrally woven therein, in accordance with the present invention. The method includes the step of providing a plurality of warp yarns 100. The method further includes the step of displacing a first group of the warp yarns 100 in a first vertical direction relative to a second group of the warp yarns 100, to create a first shed 102 between the first and second groups of warp yarns 100. This is best seen in FIG. 17C, wherein the first group of warp yarns has been designated as 104 and the second group of warp yarns has been designated as 106. The method further includes passing a weft insertion shuttle 108 through the first shed 102. This passage is performed in a first weft shuttle direction indicated by the arrow emanating from weft insertion shuttle 108, and forms a weft yarn 110.

Figure 17D:
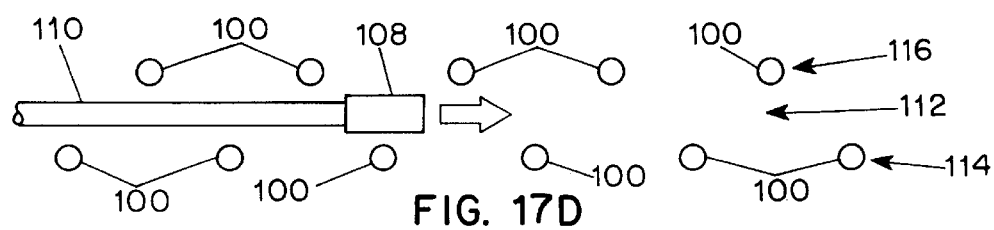

The method further includes displacing a third group of the warp yarns 100 in a second vertical direction relative to a fourth group of the warp yarns 100, so as to create a second shed 112 between the third and fourth groups of warp yarns. With reference to FIG. 17D, the third group of warp yarns is designated as 114, and the fourth group of warp yarns is designated as 116.

The method further includes passing the weft insertion shuttle 108 through the second shed 112 in a second weft shuttle direction, indicated by the arrows emanating from weft shuttle 108 in FIG. 17D, which is opposed to the first weft shuttle direction shown in FIG. 17C, to form an additional weft yarn 110. The aforementioned steps of displacing the first group of warp yarns, passing the weft insertion shuttle through the first shed, displacing the third group of warp yarns, and passing the weft insertion shuttle through the second shed can be repeated a predetermined number of times to obtain a predetermined number of the weft yarns 110. For example, with reference to FIG. 17A, the steps have been repeated so as to obtain four weft yarns 110, looking from the bottom of the figure up until the first insertion point, to be discussed next.

Figure 17E:
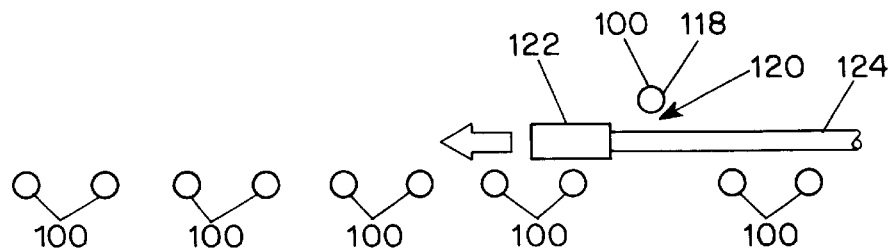
Figure 17F:
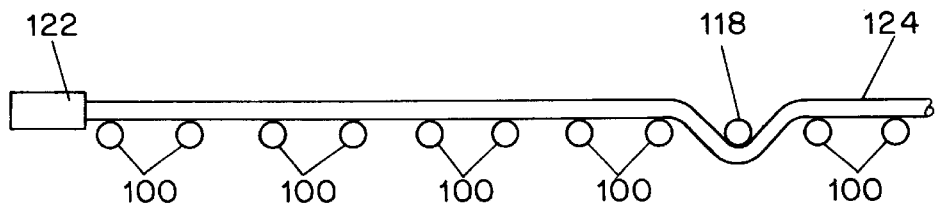

Once the predetermined number of weft yarns have been inserted, a single given warp yarn 118 can be displaced in one of the first and second vertical directions, as shown in FIG. 17E, in order to create a structural member receiving gap 120. The displacement of single given warp yarn 118 is understood to be relative to the remainder of the warp yarns 100. The method can further include passing a structural member insertion shuttle 122 through the structural member receiving gap 120 in a first horizontal direction indicated by the arrows in FIG. 17E in order to dispense a wire-like structural member 124 into the receiving gap 120. Structural member 124 could be any of the stent type structures discussed above, for example. With reference now to FIG. 17F, the method can include replacing the single given warp yarn 118 in order to secure the structural member 124.

Figure 17G:
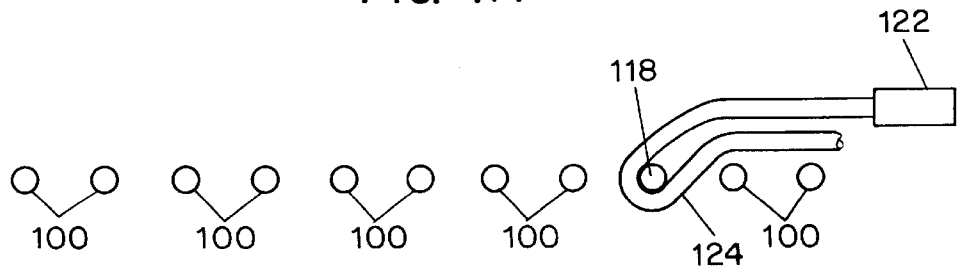

The method can further include displacing all of the warp yarns 100 in an identical vertical direction, as best seen in FIG. 17G. The displacement is conducted relative to the structural member insertion shuttle 122. The structural member insertion shuttle 122 can then be passed back past the warp yarns 100 without interweaving therewith, as also shown in FIG. 17G. With reference again now to FIG. 17A, it will be appreciated that structural member 124 has now been captured at a first interweave point 126. It should be appreciated that the method steps previously described can be carried out substantially in the order set forth. Further, the aforementioned displacement of the first group of yarns; passing of the weft insertion shuttle in the first direction; displacement of the third group of yarns; and passing of the weft shuttle in the second direction can again be repeated to obtain the predetermined number of weft yarns 110; as discussed above, the predetermined number is illustrated in FIG. 17A as four.

Further, the steps of displacing the single given warp yarn; passing the structural member insertion shuttle through the structural member receiving gap in the first direction; replacing of the single given warp yarn; displacement of all the warp yarns in the same direction; and return of the structural member insertion shuttle can be repeated with another given single warp yarn 128, as best seen in FIG. 17A. The second single given warp yarn 128 can be spaced from the first single given warp yarn 118 by a predetermined distance which, together with the predetermined number of fill yarns, defines a non-orthogonal angle α between the structural member 124 and the warp yarns 100, and which further defines a complimentary nonorthogonal angle β=90°−α between the structural member 124 and the weft yarns 110. This is best seen in FIG. 17A.

In the method, the step of providing the warp yarns 100 can include providing a first number of ordinary warp yarns selected for base textile properties and a second number of securing warp yarns, for example, yarns 118 and 128, which are used to secure the structural member 124 and which are preselected for desirable structural securing properties. The yarns can be selected as discussed above with respect to the textile.

Figure 17H:
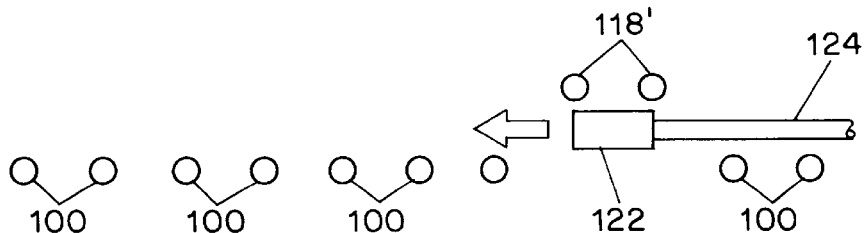
Figure 17I:
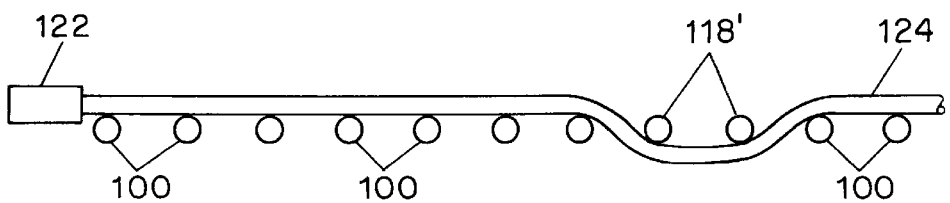

In the step of displacing the at least single given warp yarn, in order to create the structural member receiving gap, at least two adjacent warp yarns can be displaced, and then, they can both be replaced together to secure the structural member, such that the structural member 124 is secured by both of the adjacent warp yarns. The foregoing is best illustrated in FIGS. 17H and 17I, where the at least two adjacent warp yarns have been designated as 118'. It will be appreciated that the structural member 124 can be dispensed as an undulating member, or as a substantially straight member. Furthermore, when an undulating member is employed, it can be placed under sufficient tension, for example, by the structural member insertion shuttle 122, so as to substantially straighten the undulations in order to aid in inserting the structural member. The method can also, in the step of passing the structural member insertion shuttle 122 back past the warp yarns 100 without interweaving therewith, further include the sub-step of at least partially recapturing an unused portion of the structural member 124. This will be discussed and illustrated further below, with respect to a form of shuttle 122 which is adapted to carry out this task.

It should be appreciated that any desired group of the warp yarns 100 can constitute the first group which is displaced in the first vertical direction relative to the second group. Further, any desired group of the warp yarns 100 can constitute the third group which is displaced in the second vertical direction relative to the fourth group. Thus, any desired weave can be formed, including a plain weave, a satin weave, a herringbone weave, a basket weave, or any other type of weave desired. For illustrative convenience, a plain weave has been shown in the figures. It will be appreciated that, in order to form a plain weave, the first group of warp yarns displaced in the first vertical direction, that is, yarns 104, can be those of the warp yarns which are odd numbered, while the second group of warp yarns can be those which are even numbered. Further, for a plain weave, the third group and the first group will be identical and the fourth group and the second group will be identical.

Those of skill in the weaving art will appreciate that FIGS. 17A through 17I show a two-dimensional representation of the inventive weaving process, for illustrative convenience. Weaving of tubular structures is well-known in the art and the stent member or other structural member can be interwoven into such structures exactly as shown in the figures, passing the stent member on the back side of the tube for interweave points on the back side.

Figure 23A:
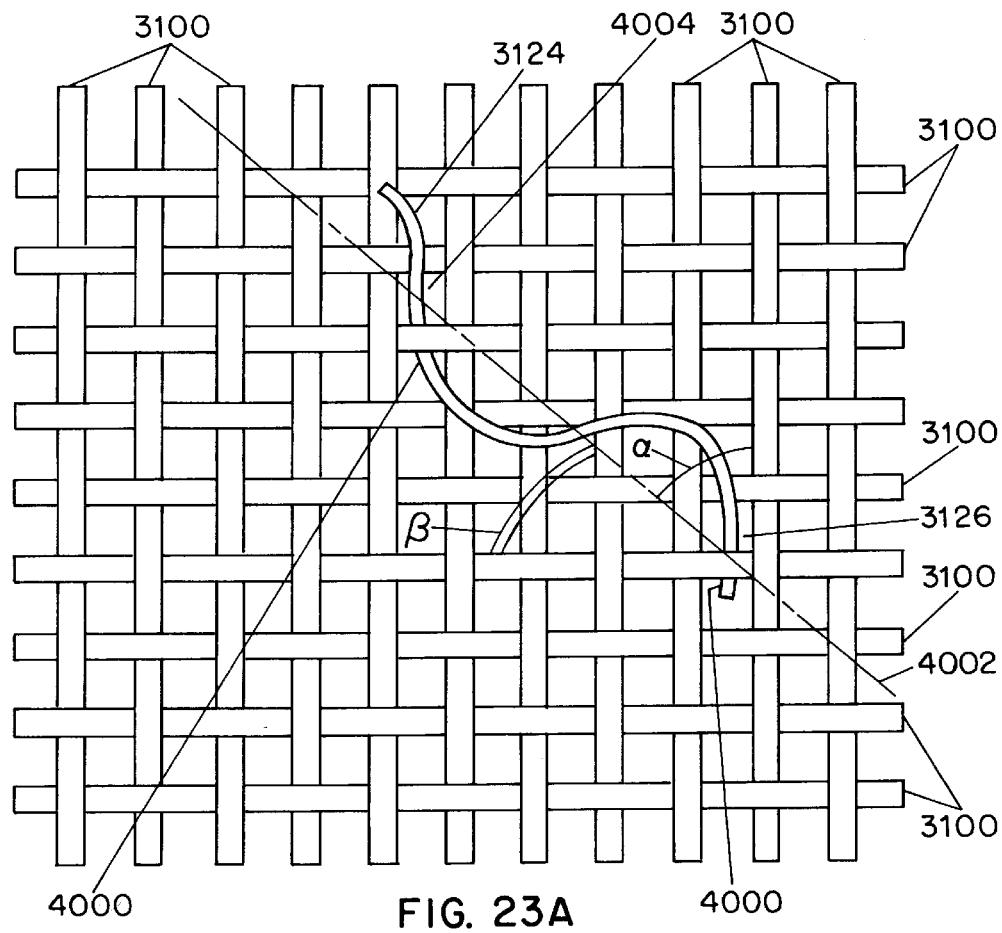
FIGS. 23A–23G show various steps in another manufacturing method according to the present invention.
Figure 23B:
Figure 23C:
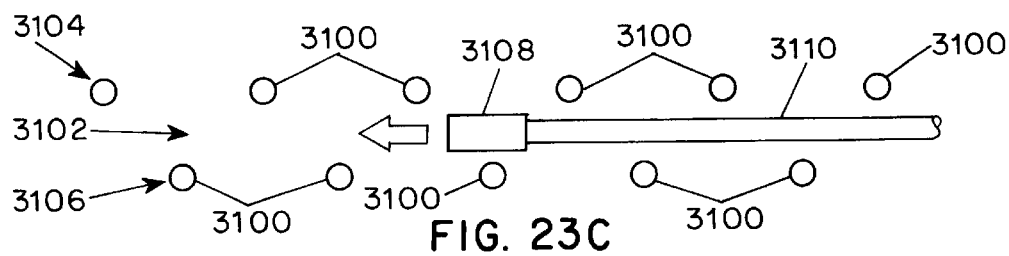

Reference should now be had to FIGS. 23A–23G which depict representative method steps of an alternative method, according to the present invention, of manufacturing a woven textile having a structural member integrally woven therein. The method includes the steps of providing a plurality of warp yarns 3100 and displacing a first group 3104 of the warp yarns 3100 in a first vertical direction relative to a second group 3106 of the warp yarns 3100, in order to create a first shed 3102 between the first and second groups of warp yarns 3104, 3106. The first shed is depicted in FIG. 23C. The method further includes passing a weft insertion shuttle 3108 through the first shed 3102, in a first weft shuttle direction, suggested by the double arrow in FIG. 23C, so as to form a weft yarn 3110. The method further includes displacing a third group 314 of the warp yarns 3100 in a second vertical direction relative to a fourth group 3116 of the warp yarns 3100, so as to create a second shed 3112 between the third and fourth groups of warp yarns 3114, 3116 respectively.

Figure 23D:
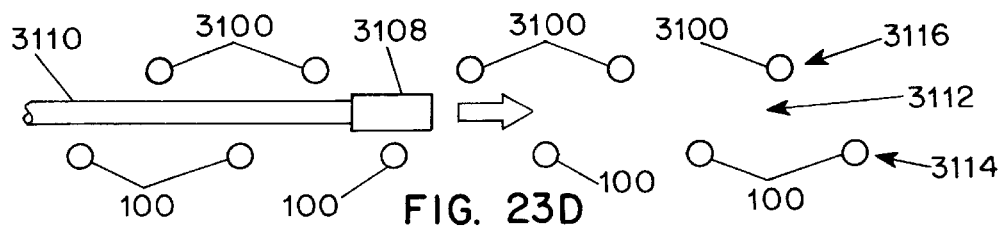
Figure 23E:
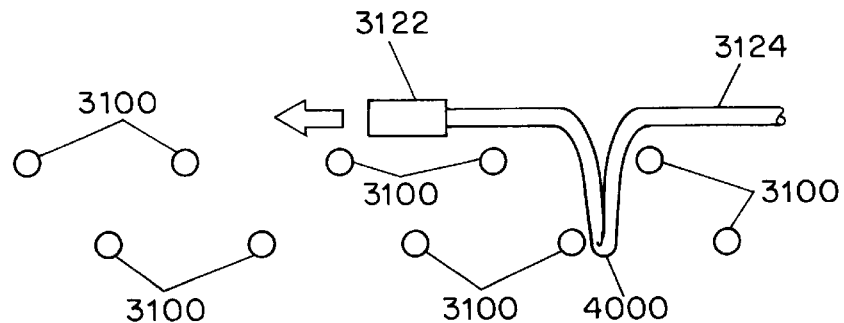
Figure 23F:
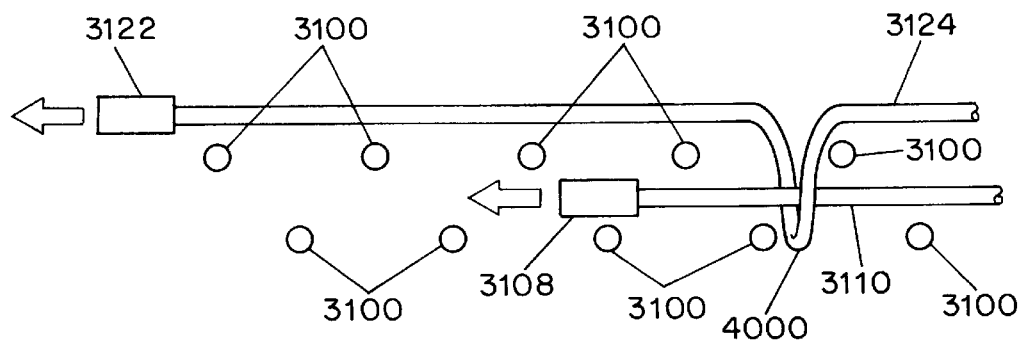
Figure 23G:
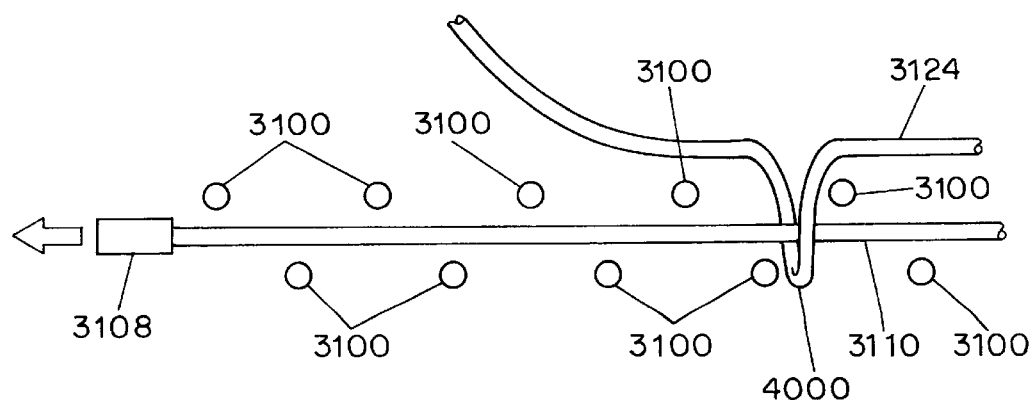

The method can further include passing the weft insertion shuttle 3108 through a second shed 3112 in a second weft shuttle direction, suggested by the double arrow in FIG. 23D, which is opposed to the first weft shuttle direction, to form an additional weft yarn 3110. All of the aforementioned steps can be repeated a predetermined number of times to obtain a predetermined number of weft yarns 3110. It will be appreciated that the foregoing description is substantially similar to that set forth above for the first method of manufacturing a woven textile. Referring now to FIG. 23E, once the previous steps have been performed, a structural member insertion shuttle 3122 can be passed across the warp and weft yarns 3100, 3110 in a first horizontal direction, signified by the double arrow in FIG. 23E, to dispense a wire-like structural member 3124. The wire-like structural member 3124 can have a plurality of recessed attachment points 4000 which are substantially parallel to the warp yarns 100, as best seen in FIG. 23A, and which are aligned with one of the first and second groups 3104, 3106 of warp yarns 3100, as best seen in FIG. 23E. As shown therein, looking end on, the recessed attachment point 4000 is substantially aligned with the second group 3104 of warp yarns 100. Structural member insertion shuttle 3122 can be "parked" (left stationary) for multiple interweaves, if desired, and can be moved (during tube weaving) as necessary to the "back" side of the tube for interweave points thereon.

Once the preceding step has been performed, one of the aforementioned steps of passing the weft insertion shuttle through the first shed in the first weft shuttle direction or through the second shed in the second weft shuttle direction can be repeated so as to secure the wire-like structural member 3124, at a given one of the attachment points 4000, with at least one weft yarn 3110. It will be appreciated that more than one weft yarn can be employed by simply making multiple passes with the weft insertion shuttle 108.

Following the preceding steps, the structural member 3124 can be displaced away from the warp and weft yarns 3100, 3110 so as to prevent any interference with subsequent weaving. This can be carried out, for example, by suitable control of the structural member 3124 with the structural member insertion shuttle 3122. Inventive shuttles which can be employed with the present invention to dispense the structural member are discussed below. A suitable weft yarn guide, such as elements 140, 140' to be discussed below, can be employed to pick up the structural member 3124 and move it out of the way of the weaving process.

At this point, the steps of displacing the first group of yarns with respect to the second group of yarns, passing the weft insertion shuttle through the first shed, displacing the third group of warp yarns with respect to the fourth group of warp yarns and then passing the weft insertion shuttle through the second shed can be repeated to again obtain the predetermined number of weft yarns 3110.

Finally, the steps of passing the structural member insertion shuttle across the warp and weft yarns, securing the wire-like structural member with a weft yarn (or yarns), and moving the structural member out of the way of the weaving process can be repeated as needed so as to secure the structural member at an additional one of the attachment points with at least an additional given weft yarn which is spaced from the at least first given weft yarn used in the initial securing step by a predetermined number of weft yarns at a location corresponding to a predetermined number of said warp yarns, such that the predetermined number of warp yarns and predetermined number of weft yarns together define a non-orthogonal angle a between a global axis 4002 (defined as above) of the structural member 3124 and the warp yarns 3100, and a complimentary non-orthogonal angle β between the global axis 4002 of the structural member 3124 and the weft yarns 3110. With particular reference to FIG. 23A, it will be appreciated that (in the example depicted therein) a first interweave point 3126 is separated from a second interweave point 4004 by two of the weft yarns 3110 which are located between the two of the weft yarns 3110 which are employed to secure the structural member 3124. Further, the weft yarns which secure the structural member 3124 do so at predetermined locations corresponding to a predetermined number of the warp yarns 3100. Still referring to FIG. 23A, the predetermined number of warp yarns between the first interweave point 3126 and the second interweave point 4004 is four. Thus, for a known spacing between the warp and between weft yarns, these predetermined number of warp and weft yarns, respectively, define the aforementioned non-orthogonal angles.

In view of the foregoing discussion with respect to FIGS. 23A–23G, it will be appreciated that the structural member 3124 could correspond to one of the aforementioned stent members and that the recessed attachment points 4000 could correspond to the aforementioned securing portions of the stent member which are positioned substantially parallel to the warp yarns 3100. Thus, one or more of the weft yarns 3110 can engage a respective one of the securing portions, for example, in the form of the recessed attachment points 4000. Further, it will be appreciated that structural member 3124 can correspond to an undulating stent and that portions of the undulations, for example, where the recessed attachment points 4000 are located, can be substantially parallel to the warp yarns 3100 and can correspond to the aforementioned plurality of securing portions. Thus, the fill or weft yarns 3110, as noted, can engage respective ones of the securing portions, for example, in the form of the recessed attachment points 4000. Thus, the aforementioned woven textile can include a structural member, such as structural member 3124, with a plurality of securing portions, for example, in the form of the recessed attachment points 4000, which are positioned substantially parallel to the warp yarns 3100 and the structural member can be integrally secured to the base fabric at a plurality of interweave points, such as interweave points 3126, 4004 by at least one fill or weft yarn 3110 engaging a respective one of the securing portions at each of the interweave points.

Figure 18:
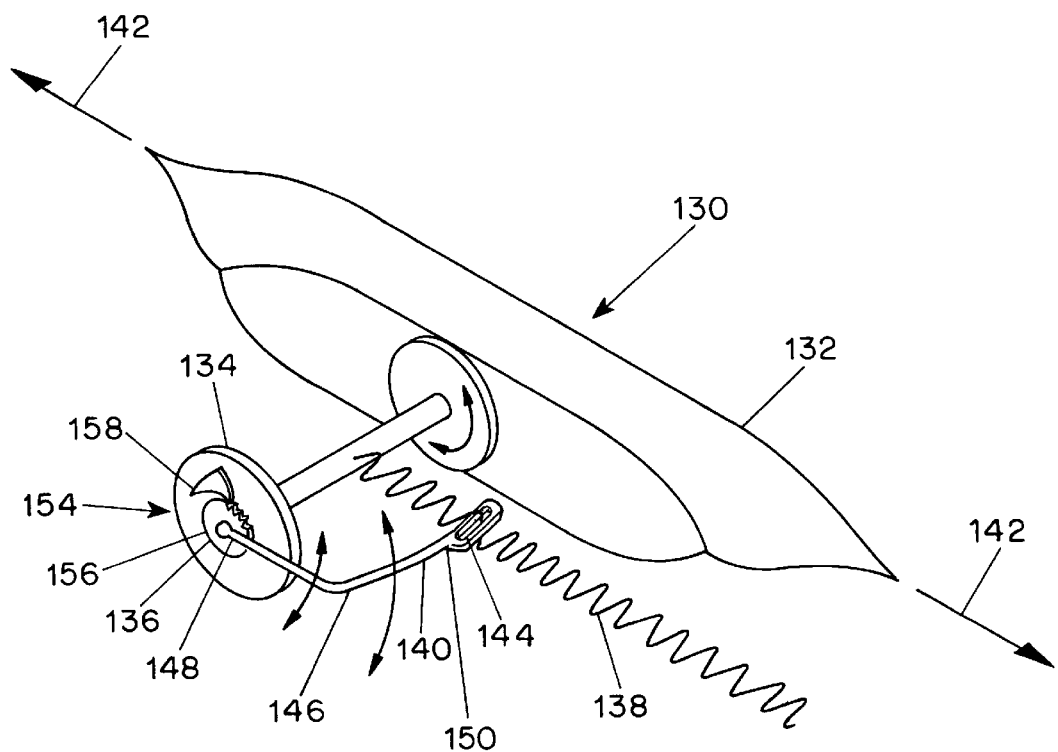
FIG. 18 shows a shuttle assembly in accordance with the present invention.

Reference should now be had to FIG. 18 which depicts a weaving shuttle designated generally as 130, in accordance with the present invention. Shuttle 130 is employed for dispensing weft yarns, such as yarns 110, when weaving with a loom. Shuttle 130 comprises a main body portion 132 which is adapted to move in a transverse direction through a shed, such as first shed 102, second shed 112, or structural member receiving gap 120, formed of warp yarns 100 on the loom. Shuttle 130 further includes a spool 134 mounted for rotation with respect to the main body portion 132 about an axis 136 which is substantially perpendicular to the transverse direction in which the main body portion 132 moves, and which is substantially parallel to the warp yarns 100.

Spool 134 is adapted to store the weft yarns 110 and to dispense the weft yarns when the main body portion 132 moves through the shed. It is to be emphasized that, in the process described above, an ordinary shuttle can ordinarily be employed to dispense the weft yarns 110, that is, for use as weft insertion shuttle 108. Shuttle 130 depicted in FIG. 18 can be employed with any type of weft yarn, but is especially adapted for dispensing the structural member, and thus, for use as the structural member insertion shuttle 122. Accordingly, an undulating structural member, which could be a stent member, designated as 138, is shown emanating from the spool 134. It will be appreciated that structural member 138 would normally have a significant portion wound about spool 134 to be dispensed; this is not shown in FIG. 18 for purposes of clarity. Shuttle 130 can further comprise a weft yarn guide 140 which is secured to the main body portion 132, for example, through the axis 136, and which is adapted to receive and guide the weft yarn, such as structural member 138, which is dispensed from the spool 134. Note that the transverse direction in which the main body portion 132 moves is suggested by arrows 142 in FIG. 18.

The weft yarn guide 140 can include an eyelet 144 which receives the weft yarn, such as structural member 138. The guide 140 can also include a cantilevered portion 146 having first and second ends 148, 150 respectively. First end 148 can be secured to the main body portion 132, for example, through the axis 136 and the second end 150 can be secured to the eyelet 144. The eyelet 144 can be dimensioned in a suitable fashion, and can have a suitable coefficient of friction, such that it receives a first frictional force applied by the weft yarn, such as the structural member 138, when the weft yarn, such as structural member 138, is being dispensed. For example, the eyelet can be made of a material such as a ceramic, which has a suitably polished finish. The eyelet can have dimensions of, for example, about 0.2 inches (about 5.1 mm) by about 0.6 inches (about 15 mm). The cantilevered portion 146 can have a span and a flexural rigidity which are selected such that the weft yarn guide 140 deflects with application of the first frictional force and recoils when the first frictional force is removed as dispensing of the weft yarns such as structural member 138 is completed.

The dimensions and coefficient of friction of the eyelet 144 can be such that it applies a second frictional force to the weft yarn, such as structural member 138, as the cantilevered portion 146 recoils, such that at least a portion of the weft yarn such as structural member 138 is recaptured. Thus, shuttle 130 can be used in carrying out the method described above wherein a portion of the structural member is recaptured. The cantilevered portion 146 can be made from an elastic material such as fiberglass, graphite composite, spring steel, multiple leaves of the same or different materials, and the like. It can have dimensions of about ¼ inch (about 6.4 mm) wide and about ⅛ inch (about 3.2 mm) thick. The exemplary dimensions are for fiberglass and they can be adjusted for materials with higher or lower values of Young's modulus to yield a comparable flexural rigidity. It will be appreciated that, as shown, cantilevered portion 146 is bent in a substantially right-angle shape, and thus comprises first and second cantilevered beams joined with rotational fixity at the apex of the angle. Any desired configuration can be employed. For the right angle shape, each beam can have a length of about 1 inch (about 25 mm).

Figure 19:
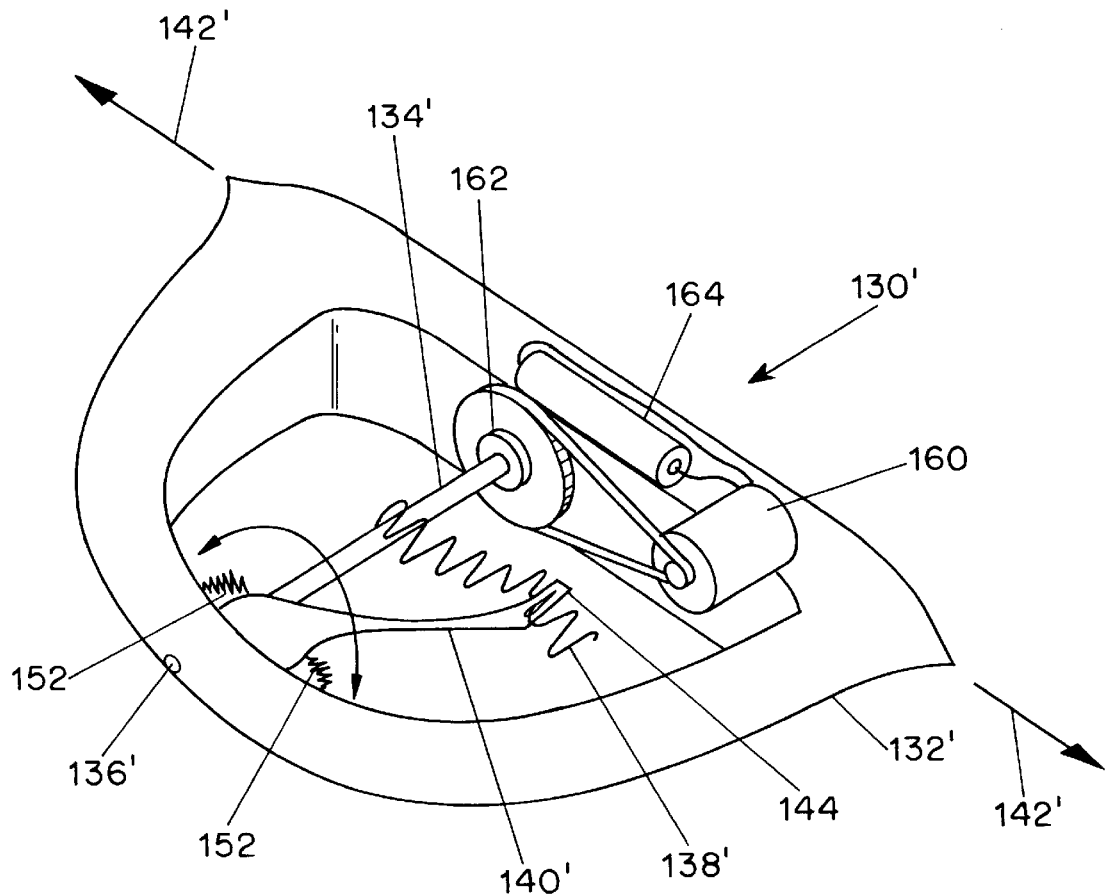
FIG. 19 shows another shuttle assembly in accordance with the present invention.

Reference should now be had to FIG. 19 which depicts an alternative form of shuttle 130' in accordance with the present invention. Components similar to those in FIG. 18 have received the same reference numeral with a "prime" thereafter. Guide 140' in the embodiment of FIG. 19 is spring loaded using suitable springs 152 which bias the guide 140' to a desired position and return it to the desired position once it has been deflected, for example, by a frictional force applied from the structural member 138'. When guide 140' is biased by the external springs 152, it need not necessarily have flexural properties, as for the cantilevered portion 146 in the embodiment of FIG. 18. It will be appreciated that one or more springs 152 can be used and can be positioned between the guide 140' and the main body 132', for example. Further, it will be appreciated that main body 132' of the embodiment shown in FIG. 19 is substantially D-shaped.

Referring now back to FIG. 18, shuttle 130 can further include an anti-reverse mechanism, designated generally as 154, which permits the spool 134 to rotate in a first rotational sense for dispensing the yarn such as structural member 138, but which prevents rotation in a second rotational sense which is opposite to the first rotational sense, that is, when the yarn is being at least partially recaptured by the weft yarn guide 140, for example. The anti reverse mechanism can include a suitable stationary gear 156 secured to axis 136 and a suitable spring-loaded pawl 158 which rotates with the spool 134 and engages the gear 156. Of course, the functions of these two components could be reversed, and the gear could instead be attached to the spool 134 with the pawl 158 mounted to an external structure and fixed with respect to the main body 132. The anti reverse mechanism 154 can be configured to apply a drag to the spool 134 to prevent the spool from overrunning when yarn such as structural member 138 is dispensed therefrom. Such a drag could be provided, for example, by the repeated engagement of the teeth of the gear 156 with the pawl 158, as is known, for example, in fishing reels.

Any of the shuttles 130, 130' can be fitted with a recapture mechanism which permits the weft yarn, such as structural member 138, 138' to be dispensed when the shuttle 130, 130' is moved in the transverse direction 142, 142' through the shed but which recaptures the unused weft yarn when the shuttle 130, 130' is moved in the transverse direction in a sense opposite to the first direction, that is, when it is desired to recapture the structural member 138, 138', as discussed above with respect to the method. Such a recapture mechanism can include the aforementioned frictional forces, eyelet and cantilevered portion shown in FIG. 18. Alternatively, with respect to FIG. 19, the recapture mechanism could include, for example, a motor 160 which is coupled to the spool 134' for rotational driving (for example, by a suitable pulley arrangement as shown). The recapture mechanism can also include a controller, such as a clutch 162 which is coupled to the motor so as to enable the rotational driving when it is desired to recapture the weft yarn, such as the structural member 138'. With reference to FIG. 19, for example, the motor 160 could turn continuously and the clutch 162 could be engaged only when it was desired to recapture the yarn, such as the structural member 138'. Motor 160 could be powered by a suitable battery 164, or using fixed leads, sliding contacts, and the like.

Figure 20:
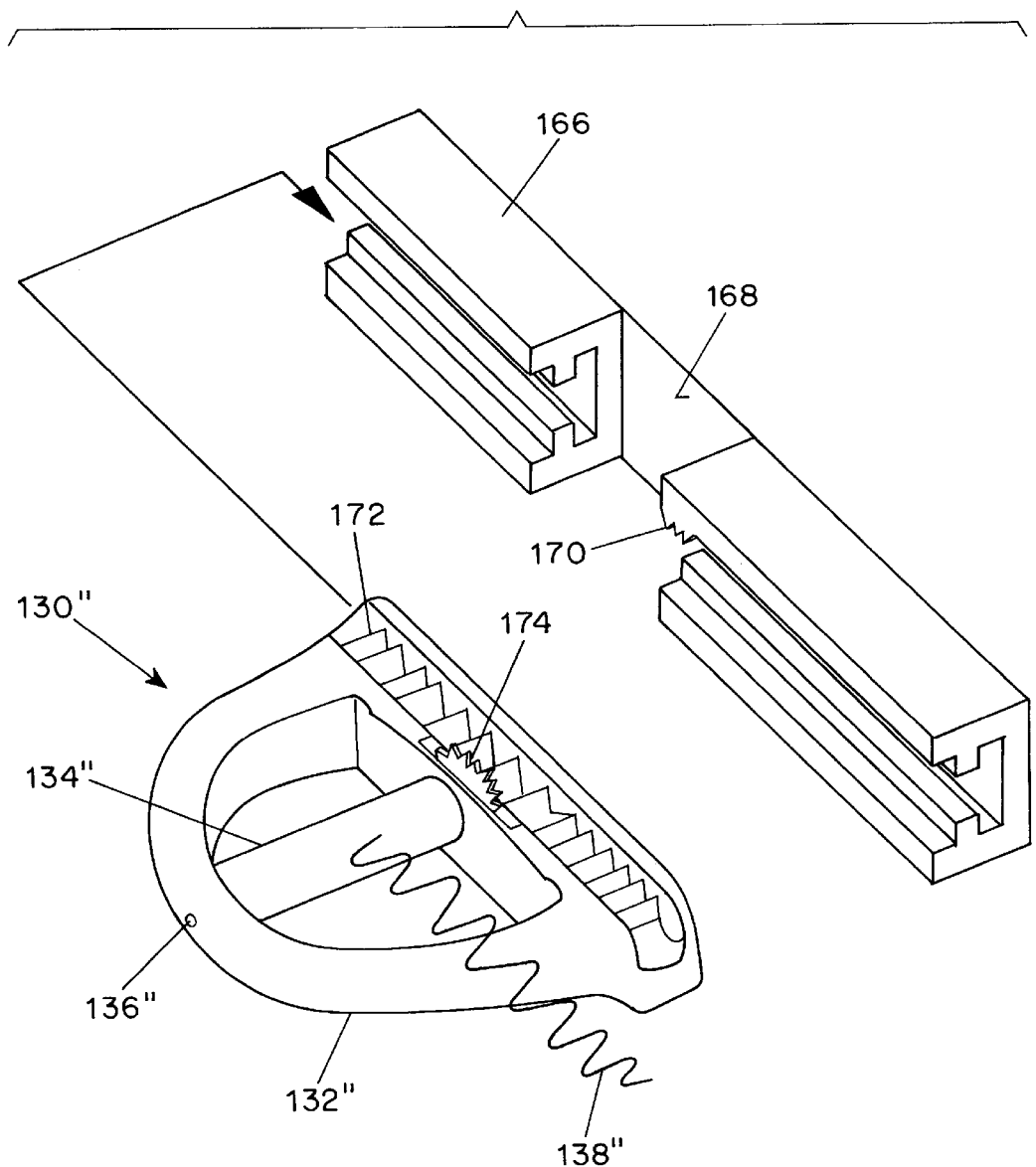
FIG. 20 shows an exploded view of yet another shuttle member in accordance with the present invention and a batten which works cooperatively with the shuttle.

Reference should now be had to FIG. 20, which depicts another embodiment of shuttle 130" in accordance with the present invention. Also shown in FIG. 20 are a shuttle slide or batten 166 and a reed 168 of a loom. Batten 166 has a rack portion thereon; for illustrative convenience, only a small segment of the rack portion 170 is shown. Shuttle 130' includes a main body 132" and a spool 134" rotating about an axis 136", similar to those described above. Main body 132" includes a shuttle rack 172, as is well known in the art, which can be used, via suitable gears, to drive the shuttle 130". Shuttle 130" further includes a pinion portion 174 which is mounted to the main body portion 132" through any suitable means, such as bearings (not shown) and which is operatively interconnected with the spool 134", for example, by being mounted on axis 136", so as to rotate the spool 134" for recapture of the unused weft yarn, such as the structural member 138" upon engagement of the pinion 174 with the rack 170 of the batten 166. A suitable clutch or other control can be employed so that rack 170 of batten 166 only causes pinion 174 to rotate spool 134" when it is desired to recapture weft yarn such as structural member 138". A suitable weft yarn guide 140 or 140', as shown above, could be adapted to the structure of FIG. 20, but is not shown for purposes of illustrative simplicity.

Figure 21:
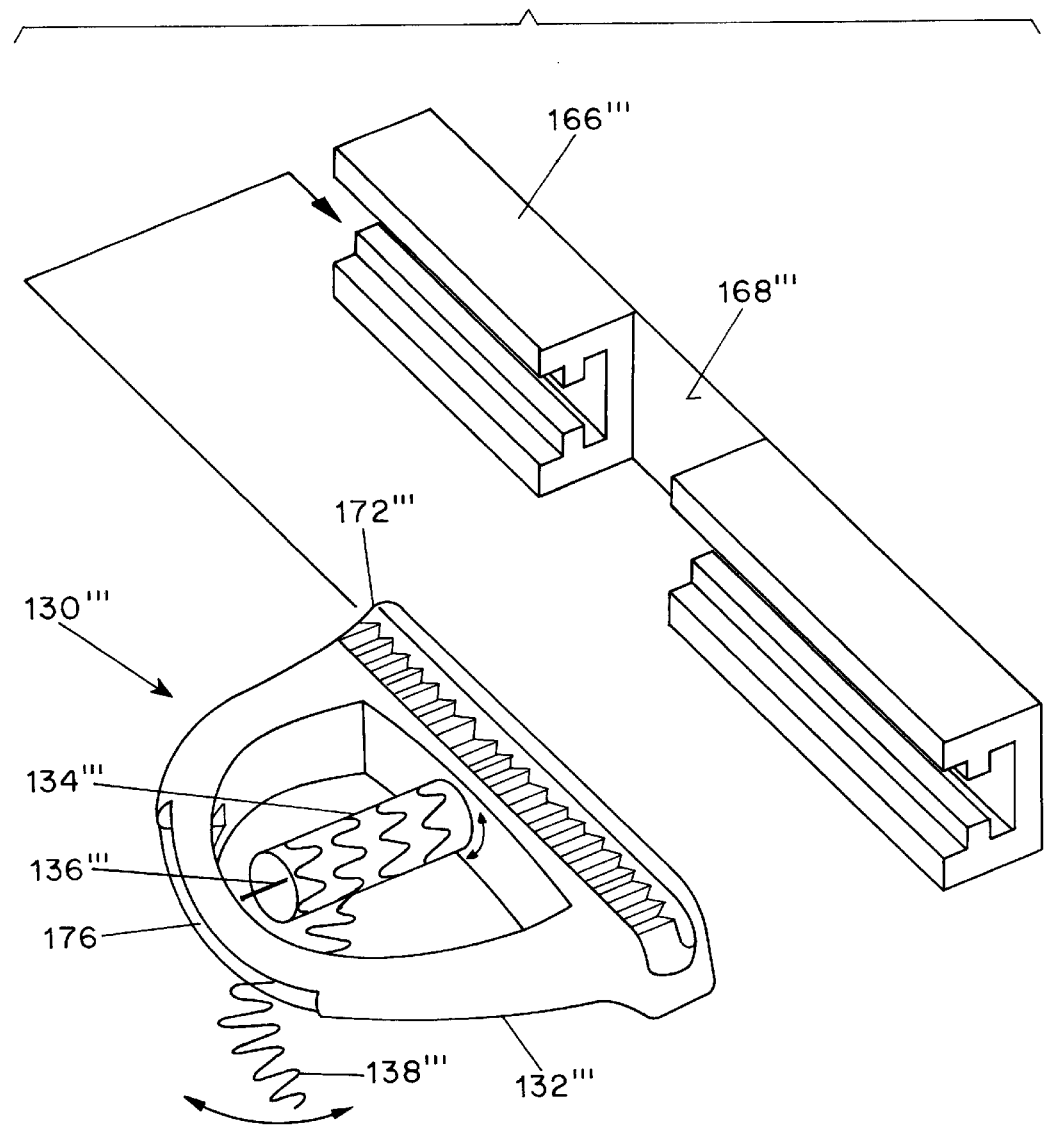
FIG. 21 is similar to FIG. 20 and shows yet another type of shuttle in accordance with the present invention.

Reference should now be had to FIG. 21 which depicts yet another embodiment of shuttle 130''' according to the present invention. Components similar to those in the preceding Figures have received the same number, followed by a triple "prime." As for the other embodiments, shuttle 130''' includes a main body portion 132''' adapted to move in a transverse direction through a shed formed of warp yarns on the loom. Also included is a spool 134''' which is mounted to the main body portion 132''' and which has an axis 136''' which is substantially perpendicular to the transverse direction in which the shuttle 130''' moves and which is substantially parallel to the warp yarns. The spool 134''' is adapted to store the weft yarn, such as structural member 138''' and to dispense the weft yarn in a direction generally parallel to the spool axis 136''' when the main body portion 132''' moves through the shed. This embodiment is similar to the so-called "spinning reel" familiar to fishermen. Spool 134''' can be stationary about axis 136''', or, if desired, can rotate thereabout, depending on twist properties which it is desired to impart to structural member 138'''. Also included is a weft yarn guide which is secured to the main body portion 132''' and which is positioned to receive the weft yarn, such as structural member 138''', as it is dispensed from the spool 134'''. As shown in FIG. 21, the weft yarn guide can simply be a slot 176 which is formed in the main body portion 132''' and which receives the structural member 138''' (or other weft yarn). It will be appreciated that the guide, such as slot 176, guides the weft yarn 138''' into a direction which is substantially parallel to the transverse direction in which the main body portion 132''' moves. In the embodiment shown in FIGS. 20 and 21, it is to be appreciated that the main body portion 132", 132''' rides in the corresponding grooves formed in the batten 166, 166". Although any of the embodiments can be employed with any structural member desired, it is believed that the embodiment shown in FIG. 21 has special utility with structural members formed on the mandrel shown in FIGS. 15A and 15B.

Any suitable type of loom can be employed using the inventive shuttles of the present invention. The warp yarn can be tensioned, for example, using the so-called drop-weight system of let-off, as is known in the art.

Figure 22:
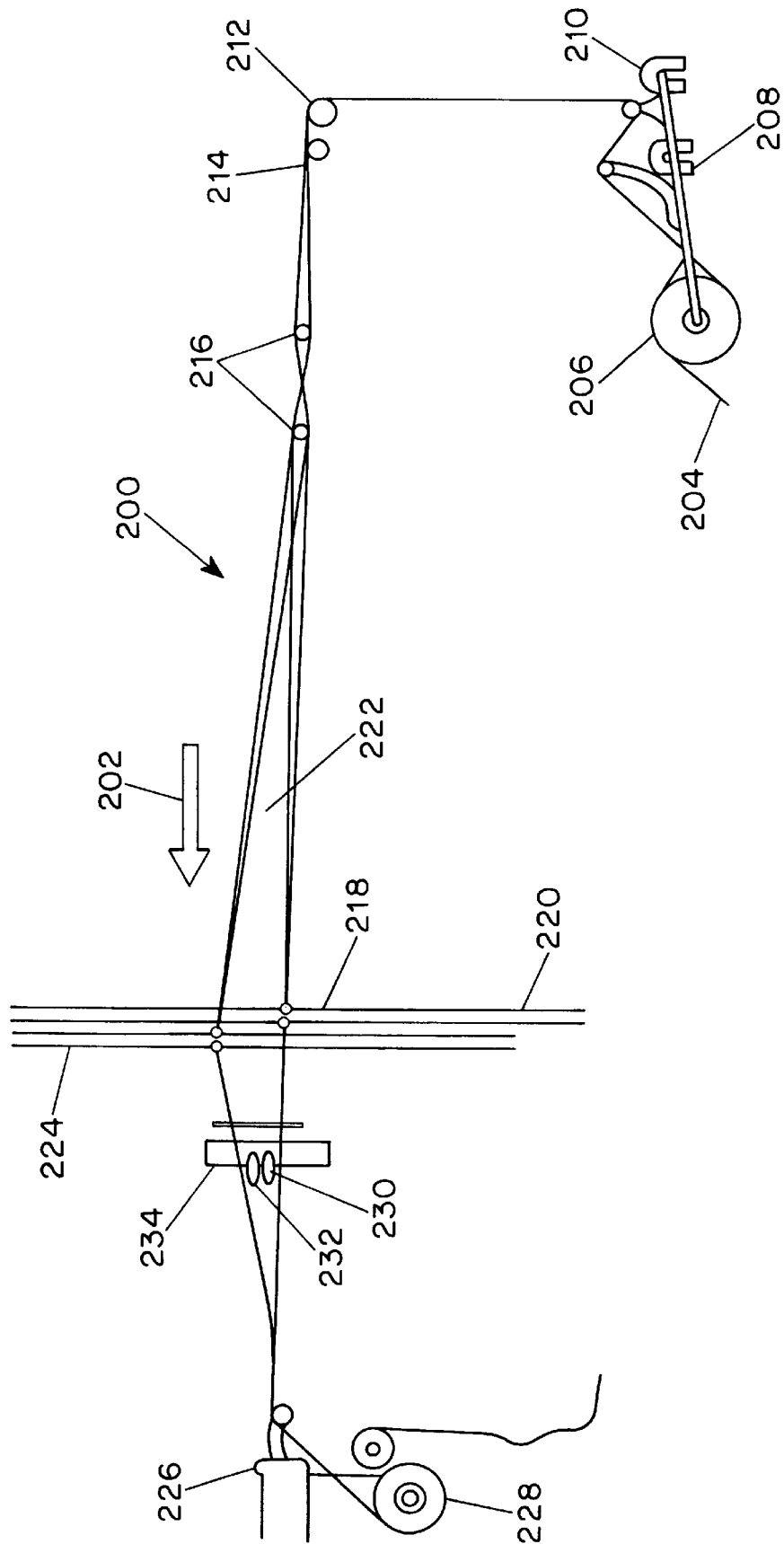
FIG. 22 is a side elevational view of a loom employing multiple shuttles according to the present invention.

Attention should now be given to FIG. 22 which depicts a typical loom set up to manufacture products according to the present invention using methods according to the present invention. The loom, designated generally as 200, weaves fabric in a direction indicated by arrow 202. Loom 200 includes a beam strap 204, warp beam 206, let-off brackets 208 and warp tension weights 210, as known in the art. A suitable whip roll 212, warp sheet 214, lease rods 216, heddle 218 and lingoe 220 are also shown. A warp shed 222 is depicted. A raised harness, suitable for displacing warp yarns as discussed above, is shown at 224. A breast beam is depicted at 226 and a take up roll is shown at 228. First and second shuttles 230, 232 ride in batten 234, one above the other. One of the shuttles 230, 232 can be used for the ordinary weft yarns, while another of the shuttles 230, 232 can be used for the stent or structural members, as discussed above. For the composite type embodiments, where multiple structural or stent members are used, additional shuttles can be added as required.

Diameters of tubular stent/graft structures, for medical applications, according to the present invention can range from about 2 mm to about 50 mm, although these dimensions are exemplary and should not be taken as limiting. Larger diameters can be made for industrial applications, as desired. Four harnesses 224 can be used to weave a simple double cloth fabric tube. Additional harnesses can be used to control interweaving. A rapier loom can be used for weaving flat fabrics.

EXAMPLE

Tubular grafts, in accordance with the present invention, were prepared in the configuration shown in FIG. 1. The textile graft 12 was a ground weave plain lattice structure. The warp ground was 50/68 microdenier texturized unshrunk polyester. Six stent-securing interweave warp yarns were employed at each interweave point; these were two-plied yarns made from two individual 50/68 microdenier 8z texturized unshrunk polyester yarns. The fill yarn was 50/68 microdenier 8z texturized unshrunk polyester. The weave density for the finished fabric was 100 ends per inch, 118 picks per inch. The tubular graft 12 had a Griege inside diameter of 19 mm and a finished inside diameter of 18 mm.

The wire stent material was 0.011 inch (0.28 mm) diameter as-drawn Nitinol shaped in a sinusoidal pattern using an aluminum mandrel of the type shown in FIGS. 15A and 15B. The Nitinol shaping temperature was about 500 to about 560 degrees C with dwell times ranging from about 1 to about 5 minutes. A shaping temperature of 540 degrees C was found to be preferable.

Eight interweave points were spaced equally about the circumference of the graft and were repeated axially as needed. A helix angle of about 83 degrees was employed as defined in FIG. 3 for the stent member global axis. Eight pick yarns separated each interweave point.

The radial force which can be developed and the ability to self-support can be controlled by varying the helix angle and wire diameter. Increasing either or both of these parameters increases the amount of radial force. Reduced microdenier yarn twist can result in a denser, less permeable fabric.

After weaving, the stent/graft structure with interwoven wire was scoured to remove any possible contamination from weaving and yarn sizing. The structure was then loaded on a cylindrical mandrel and heat set in a convection oven for 30 minutes at 130 degrees C. Heat setting results in a three-dimensional shape-retaining fabric, but does not change the elastic properties of the stent member. The dimensions, materials and other parameters set forth in the preceding example are those currently believed preferable, but should not be taken as limiting. For example, it is presently believed that 30 Denier yarns may prove desirable for some medical applications.

While there have been described what are presently believed to be the preferred embodiments of the invention, those skilled in the art will realize that various changes and modifications may be made to the invention without departing from the spirit of the invention, and it is intended to claim all such changes and modifications as fall within the scope of the invention.

What is claimed is:

1. A combined stent/graft structure for repair of a body tube in a living body, the body tube having an inner surface, said combined stent/graft structure comprising:

a textile graft adapted to enhance fluid integrity of the body tube, said graft having a generally tubular graft main portion with a graft main portion axis and first and second graft main portion ends, said graft main portion being formed, at least in part, by at least one graft yarn; and a stent expandable between a first position permitting easy insertion of said stent into the body tube and a second position wherein said stent presses securely against the inner surface of the body tube, said stent in turn comprising a first elongate wire-shaped stent member having both a first stent member global axis and a first stent member local axis, said first stent member being integrally secured to said graft by said at least one graft yarn of which said graft is formed, substantial portions of said first stent member global axis forming a non-orthogonal angle with said graft main portion axis when projected into a plane containing said graft main portion axis, said first stent member having material properties preselected to support said graft when in said second position, said first stent member local axis being generally defined by centroids of adjacent cross-sections of said first stent member, said first stent member global axis being generally defined by a straight-line curve fit to said first stent member local axis in a coordinate system substantially coincident with said generally tubular graft main portion.

2. The structure of claim 1, wherein said textile graft is woven.

3. The structure of claim 2, wherein:

said first stent member local axis and said first stent member global axis are substantially coincident; and said non-orthogonal angle is a helix angle selected to permit said first stent member to extend substantially between said first and second graft main portion ends and to obtain substantially homogeneous compressive and flexural properties for said combined stent/graft structure.

4. The structure of claim 3, wherein said helix angle ranges from about 10 degrees to about 85 degrees.

5. The structure of claim 3, wherein said helix angle ranges from about 45 degrees to about 85 degrees.

6. The structure of claim 2, wherein said first stent member local axis defines a plurality of undulations extending on first and second sides of said first stent member global axis.

7. The structure of claim 6, wherein:

said woven graft is formed from a plurality of warp yarns and a plurality of fill yarns which are substantially orthogonal to said plurality of warp yarns;

said at least one graft yarn which integrally secures said first stent member is at least one of:

said plurality of warp yarns; and said plurality of fill yarns;

said plurality of undulations are substantially periodic about said first stent member global axis; and said first stent member global axis is substantially non-orthogonal to both said plurality of warp yarns and said plurality of fill yarns.

8. The structure of claim 7, wherein said non-orthogonal angle which said first stent member global axis forms with said graft main portion axis is a helix angle selected to permit said first stent member to extent substantially between said first and second graft main portion ends and to obtain substantially homogeneous compressive and flexural properties for said combined stent/graft structure.

9. The structure of claim 8, wherein said helix angle ranges from about 10 degrees to about 85 degrees.

10. The structure of claim 8, wherein said helix angle ranges from about 45 degrees to about 85 degrees.

11. The structure of claim 7, wherein said first stent member is a wire formed from a ductile material which undergoes plastic deformation induced by a separate expanding force in expanding from said first position to said second position.

12. The structure of claim 7, wherein said first stent member is a wire formed from an elastic material which undergoes substantially elastic deformation in expanding from said first position to said second position and wherein said first stent member expands between said first and second positions at least substantially via stored energy released upon removal of an external constraint.

13. The structure of claim 7, wherein said first stent member is integrally secured to said graft at a plurality of interweave points, said first stent member being secured by at least one warp yarn at each of said interweave points, adjacent interweave points being separated by a predetermined number of said fill yarns and a predetermined number of said warp yarns which together define a substantially non-orthogonal angle $\alpha$ which said first stent member global axis forms with said plurality of warp yarns and a complementary substantially non-orthogonal angle $\beta=9°-\alpha$ which said first stent member global axis forms with said plurality of fill yarns.

14. The structure of claim 13, wherein said plurality of warp yarns comprise:

a first group of warp yarns which are not employed at said interweave points and which are selected for desired graft properties;

a second group of warp yarns employed at said interweave points and having properties selected for securing said first stent member.

15. The structure claim 13, wherein said first stent member is secured by at least two warp yarns at each of said interweave points.

16. The structure of claim 7, wherein said first stent member has a plurality of securing portions which are positioned substantially parallel to said warp yarns and wherein said stent member is integrally secured to said graft at a plurality of interweave points, said first stent member being secured by at least one weft yarn engaging a respective one of said securing portions at each of said interweave points, adjacent interweave points being separated by a predetermined number of said fill yarns and a predetermined number of said warp yarns which together define a substantially non-orthogonal angle a which said first stent member global axis forms with said plurality of warp yarns and a complementary substantially non-orthogonal angle $\beta=90°-\alpha$ which said first stent member global axis forms with said plurality of fill yarns.

17. The structure of claim 1, wherein:

said textile graft is bifurcated and further comprises first and second secondary portions emanating from said second graft main portion end in a substantially fluid-integrity-enhancing fashion, said first and second secondary portions being generally tubular and having first and second secondary portion axes respectively, said first secondary portion being formed at least in part by at least one first secondary portion yarn, said second secondary portion being formed, at least in part, by at least one second secondary portion yarn;

said stent further comprises a second elongate wire-shaped stent member having both a second stent member global axis and a second stent member local axis, said second stent member also being integrally secured to said graft by said at least one graft yarn of which said graft is formed, substantial portions of said second stent member global axis forming a non-orthogonal angle with said graft main portion axis when projected into a plane containing said graft main portion axis, said second stent member having material properties preselected to support said graft when in said second position, said second stent member local axis being generally defined by centroids of adjacent cross-sections of said second stent member, said second stent member global axis being generally defined by a straight-line curve fit to said second stent member local axis in a coordinate system substantially coincident with said generally tubular graft main portion;

said first and second stent members are both present in said graft main portion;

said first stent member is integrally secured to said first secondary portion by said at least one first secondary portion yarn, substantial portions of said first stent member global axis forming a non-orthogonal angle with said first secondary portion axis when projected into a plane containing said first secondary portion axis;

said second stent member is integrally secured to said second secondary portion by said at least one second secondary portion yarn, substantial portions of said second stent member global axis forming a non-orthogonal angle with said second secondary portion axis when projected into a plane containing said second secondary portion axis.

18. The structure of claim 17, wherein said first and second stent members are axially spaced in said graft main portion and form a substantially double helical structure therein.

19. The structure of claim 17, wherein said first and second stent members are substantially coextensive in said main graft portion.

20. The structure of claim 1, wherein said first stent member extends substantially from said first graft main portion end to said second graft main portion end.

21. The structure of claim 1, wherein said graft main portion tapers from said first graft main portion end to said second graft main portion end.

22. The structure of claim 1, wherein said first stent member is formed of an elastic material selected for flexible self-support of said graft main portion and wherein said first stent member extends along said graft main portion but terminates before reaching at least one of said first and second graft main portion ends;

said structure further comprising at least a second stent member formed of a ductile material selected for apposition of the body tube inner surface by balloon expansion, said second stent member being located at said at least one of said first and second graft main portion ends which said first stent member terminates before reaching, said second stent member being integrally secured to said graft by said at least one graft yarn of which said graft is formed.

23. A combined stent/graft structure for repair of a body tube in a living body, the body tube having an inner surface, said combined stent/graft structure comprising:

a woven graft adapted to enhance fluid integrity of the body tube, said graft having a generally tubular graft main portion with a graft main portion axis and first and second graft main portion ends, said graft being formed from a plurality of warp yarns and a plurality of fill yarns which are substantially orthogonal to said plurality of warp yarns; and a stent expandable between a first position permitting easy insertion of said stent into the body tube and a second position wherein said stent presses securely against the inside surface of the body tube, said stent in turn comprising a first elongate wire-shaped stent member having a plurality of undulations, said first stent member being integrally secured to said graft at a first plurality of interweave points, said first stent member being secured by at least one warp yarn at each of said first plurality of interweave points, said first plurality of interweave points being spaced circumferentially about said graft and being separated from each other by a predetermined number of said warp yarns.

24. The structure of claim 23, wherein said plurality of warp yarns comprise:

a first group of warp yarns which are not employed at said interweave points and which are selected for desired graft properties;

a second group of warp yarns employed at said interweave points and having properties selected for securing said first stent member.

25. The structure claim 23, wherein said first stent member is secured by at least two warp yarns at each of said interweave points.

26. The structure of claim 23, wherein:

said first plurality of interweave points have a first substantially identical axial coordinate; and said first stent member is also secured to said graft at a second plurality of interweave points having a second substantially identical axial coordinate, said first plurality of interweave points and said second plurality of interweave points being separated by a predetermined number of said fill yarns.

27. A combined stent/graft structure for repair of a body tube in a living body, the body tube having an inner surface, said combined stent/graft structure comprising:

a woven graft adapted to enhance fluid integrity of the body tube, said graft having a generally tubular graft main portion with a graft main portion axis and first and second graft main portion ends, said graft being formed from a plurality of warp yarns and a plurality of fill yarns which are substantially orthogonal to said plurality of warp yarns; and a stent expandable between a first position permitting easy insertion of said stent into the body tube and a second position wherein said stent presses securely against the inside surface of the body tube, said stent in turn comprising a first elongate wire-shaped stent member having a plurality of undulations, portions of said undulations being substantially parallel to said warp yarns at a plurality of securing portions, said first stent member being integrally secured to said graft at a first plurality of interweave points, said first stent member being secured by at least one fill yarn engaging a respective one of said securing portions at each of said first plurality of interweave points, said first plurality of interweave points being spaced circumferentially about said graft and being separated from each other by a predetermined number of said warp yarns.

28. A woven textile comprising:
(a) a plurality of warp yarns;
(b) a plurality of fill yarns which are substantially orthogonal to said plurality of warp yarns and form a base fabric therewith; and
(c) an elongate wire-shaped structural member having both a member global axis and a member local axis, said member local axis being generally defined by centroids of adjacent cross-sections of said structural member, said member global axis being generally defined by a straight-line curve fit to said member local axis in a coordinate system which is substantially coplanar with said warp and fill yarns, said structural member being integrally secured to said base fabric at a plurality of interweave points, said member being secured by at least one warp yarn at each of said interweave points, adjacent interweave points being separated by a predetermined number of said fill yarns and a predetermined number of said warp yarns which together determine a substantially non-orthogonal angle a between said member global axis and said warp yarns and a complimentary substantially non-orthogonal angle $\beta=90°-\alpha$ between said member global axis and said fill yarns.

29. The woven textile of claim 28, wherein:
said structural member local axis and said structural member global axis are substantially coincident; and
said non-orthogonal angle $\alpha$ ranges from about 10 degrees to about 85 degrees.

30. The woven textile of claim 28, wherein:
said structural member local axis and said structural member global axis are substantially coincident; and
said non-orthogonal angle $\alpha$ ranges from about 45 degrees to about 85 degrees.

31. The woven textile of claim 28, wherein said structural member local axis defines a plurality of undulations extending on first and second sides of said structural member global axis.

32. The woven textile of claim 31, wherein said plurality of undulations are substantially periodic about said structural member global axis.

33. The woven textile of claim 28, wherein said plurality of warp yarns comprise:
a first group of warp yarns which are not employed at said interweave points and which are selected for desired base fabric properties; and
a second group of warp yarns employed at said interweave points and having properties selected for securing said structural member.

34. The woven textile of claim 28, wherein said structural member is secured by at least two warp yarns at each of said interweave points.

35. A woven textile comprising:
(a) a plurality of warp yarns;
(b) a plurality of fill yarns which are substantially orthogonal to said plurality of warp yarns and form a base fabric therewith; and
(c) an elongate wire-shaped structural member having both a member global axis and a member local axis, said member local axis being generally defined by centroids of adjacent cross-sections of said structural member, said member global axis being generally defined by a straight-line curve fit to said member local axis in a coordinate system which is substantially coplanar with said warp and fill yarns, said structural member having a plurality of securing portions which are positioned substantially parallel to said warp yarns, said structural member being integrally secured to said base fabric at a plurality of interweave points, said member being secured by at least one fill yarn engaging a respective one of said securing portions at each of said interweave points, adjacent interweave points being separated by a predetermined number of said fill yarns and a predetermined number of said warp yarns which together determine a substantially non-orthogonal angle a between said member global axis and said warp yarns and a complimentary substantially non-orthogonal angle $\beta=90°-\alpha$ between said member global axis and said fill yarns.

36. The structure of claim 1, 2, 17 or 22, wherein said textile graft is comprised at least in part of microdenier yarns.

37. The structure of claim 7, wherein at least one of said warp yarns and said fill yarns is comprised at least in part of microdenier yarns.

38. The structure of claim 37, wherein both said warp yarns and said fill yarns are comprised at least in part of microdenier yarns.

39. The structure of claim 23 or 27, wherein at least one of said warp yarns and said fill yarns is comprised at least in part of microdenier yarns.

40. The structure of claim 39, wherein both said warp yarns and said fill yarns are comprised at least in part of microdenier yarns.

41. The woven textile of claim 31 or 38, wherein at least one of said warp yarns and said fill yarns is comprised at least in part of microdenier yarns.

42. The woven textile of claim 41, wherein both said warp yarns and said fill yarns are comprised at least in part of microdenier yarns.

* * * * *

UNITED STATES PATENT AND TRADEMARK OFFICE
CERTIFICATE OF CORRECTION

PATENT NO. : 6,159,239
DATED : December 12, 2000
INVENTOR(S) : Greenhalgh

Page 1 of 2

It is certified that error appears in the above-identified patent and that said Letters Patent is hereby corrected as shown below:

Column 3,
Line 28, "complimentary" should read -- complementary --

Column 4,
Line 8, "complimentary" should read -- complementary --

Column 7,
Line 36, "as" should read -- is --

Column 9,
Line 37, "complimentary" should read -- complementary --

Column 15,
Line 49, "complimentary" should read -- complementary --

Column 17,
Line 65, "complimentary" should read -- complementary --

Column 20,
Line 9, "complimentary" should read -- complementary --

Column 26,
Line 32, "$\beta=9°-\alpha$" should read -- $\beta=90°-\alpha$ --
Line 39, "properties;" should read -- properties; and --
Line 57, "a" should read -- $\alpha$ --

Column 27,
Line 31, "axis;" should read -- axis; and --

Column 28,
Line 28, "properties;" should read -- properties; and

UNITED STATES PATENT AND TRADEMARK OFFICE
CERTIFICATE OF CORRECTION

PATENT NO. : 6,159,239
DATED : December 12, 2000
INVENTOR(S) : Greenhalgh

It is certified that error appears in the above-identified patent and that said Letters Patent is hereby corrected as shown below:

Column 29,
Line 24, "a" should read -- α --
Line 25, "complimentary" should read -- complementary --

Column 30,
Line 27, "a" should read -- α --
Line 28, "complimentary" should read -- complementary --

Signed and Sealed this

First Day of January, 2002

Attest:

JAMES E. ROGAN
*Attesting Officer*    *Director of the United States Patent and Trademark Office*